US006207384B1

(12) United States Patent
Mekalanos et al.

(10) Patent No.: US 6,207,384 B1
(45) Date of Patent: Mar. 27, 2001

(54) SYSTEMATIC IDENTIFICATION OF ESSENTIAL GENES BY IN VITRO TRANSPOSON MUTAGENESIS

(75) Inventors: John J. Mekalanos, Cambridge; Brian J. Akerley, Brookline; Eric J. Rubin, Waban; Andrew Camilli, Sharon, all of MA (US)

(73) Assignees: The General Hospital Corporation; Trustees of Tufts College, both of Boston; President and Fellows of Harvard College, Cambridge, all of MA (US)

( * ) Notice: Subject to any disclaimer, the term of this patent is extended or adjusted under 35 U.S.C. 154(b) by 0 days.

(21) Appl. No.: 09/277,565

(22) Filed: Mar. 26, 1999

Related U.S. Application Data

(60) Provisional application No. 60/079,770, filed on Mar. 27, 1998.

(51) Int. Cl.$^7$ .............................. C12Q 1/02; C12Q 1/68; C12N 15/74; C12N 15/63; C12N 15/85

(52) U.S. Cl. ................................ 435/6; 435/473; 435/29; 435/468; 435/455; 435/91.2; 536/23.1

(58) Field of Search ................................ 435/6, 29, 7.32, 435/473, 468, 455, 243; 536/23.1

(56) References Cited

U.S. PATENT DOCUMENTS

| | | | | |
|---|---|---|---|---|
| 5,173,294 | | 12/1992 | Murphy et al. | 424/139.1 |
| 5,612,180 | * | 3/1997 | Brown et al. | 435/6 |
| 5,792,633 | | 8/1998 | Schiestl et al. | 435/6 |
| 5,817,502 | | 10/1998 | Ligon et al. | 435/252.34 |
| 5,843,772 | | 12/1998 | Devine et al. | 435/320.1 |

OTHER PUBLICATIONS

Akerley et al., "Systematic identification of essential genes by in vitro *mariner* mutagenesis," Proc. Natl. Acad. Sci. 95:8927–8932 (1998).

Alexeyev et al., "Improved antibiotic–resistance gene cassettes and omega elements for *Escherichia coli* vector construction and in vitro deletion/insertion," Gene 160:63–67 (1995).

Barcak et al., "Genetic Systems in *Haemophilus influenzae*," Methods in Enzymology 204:321–342 (1991).

Claverys et al., "Construction and evaluation of new drug–resistance cassettes for gene disruption mutagenesis in *Streptococcus pneumoniae,* using an ami test platform," Gene 164:123–128 (1995).

Gwinn et al., "In vitro Tn7 mutagenesis of *Haemophilus influenzae* Rd and characterization of the role of atpA in transformation," Journal of Bacteriology 179:7315–7320 (1997).

Havarstein et al., "An unmodified heptadecapeptide pheromone induces competence for genetic transformation in *Streptococcus pneumoniae*," Proc. Natl. Acad. Sci. USA 92:11140–11144 (1995).

Herriott et al., "Defined Nongrowth Media for Stage II Development of Competence in *Haemophilus influenzae*," J. Bacteriol. 101:517–524 (1970).

Kurtz et al., "Growth Impairment Resulting from Expression of Influenza Virus M2 Protein in *Saccharomyces cerevisiae:* Identification of a Novel Inhibitor of Influenza Virus," Antimicrobial Agents and Chemotherapy 39:2204–2209 (1995).

(List continued on next page.)

*Primary Examiner*—David Guzo
*Assistant Examiner*—Gerald G. Leffers, Jr.
(74) *Attorney, Agent, or Firm*—Clark & Elbing LLP; Kristina Bieker-Brady

(57) ABSTRACT

The invention features a general system for the identification of essential genes in organisms. This system is applicable to the discovery of novel target genes for antimicrobial compounds, as well as to the discovery of genes that enhance cell growth or viability.

22 Claims, 24 Drawing Sheets

OTHER PUBLICATIONS

Lampe et al., "A purified *mariner* transposase is sufficient to mediate transposition in vitro," EMBO J. 15:5470–5479 (1996).

Reidl et al., "Lipoprotein e(p4) is Essential for Hemin Uptake by *Haemophilus influenzae*," J. Exp. Med. 183:621–629 (1996).

Rubin et al., "In vivo transposition of *mariner*–based elements in enteric bacteria and mycobacteria," Proc. Natl. Acad. Sci. USA 96:1645–1650 (1999).

Schmidt et al., "SecA Protein Autogenously Represses Its Own Translation during Normal Protein Secretion in *Escherichia coli*," Journal of Bacteriology 171:643–649 (1989).

Shoemaker et al., "Destruction of Low Efficiency Markers is a Slow Process Occurring at a Heteroduplex Stage of Transformation," Mol. Gen. Genet. 128:283–290 (1974).

Singh et al., "High–resolution functional mapping of a cloned gene by genetic footprinting," Proc. Natl. Acad. Sci. USA 94:1304–1309 (1997).

Smith et al., "Genetic footprinting: A genomic strategy for determining a gene's function given its sequence," Proc. Natl. Acad. Sci USA 92:6479–6483 (1995).

* cited by examiner

HI0455

ATGACCGCACTTTACCCTTGGCTAATGCCAATTTATCATCAAATTGCTCAAACCTTTGACGAAGGGTTGG
GGCATCATGCTGTGCTGATTAAAGCTGATTCTGGTTTAGGCGTAGAGAGTTTATTTAATGCACTTGCACA
GAAAATAATGTGTGTAGCTCAAGGCGATAAACCTTGTGGTCAATGCCATTCTTGTCATTTAATGCAAGCC
CATAGCCATCCAGATTATCACGAATTAAGCCCCATTAACGGTAAGGATATTGGCGTTGATCAAGTACGCG
ACATTAATGAAATGGTTGCGCAGCACGCACAACAAAACGGCAATAAAGTGGTGTATGTGCAAGGGGCGGA
ACGTTTAACGGAAGCGGCTGCTAATGCATTATTGAAAACATTGGAAGAGCCTCGTCCAAATACTTATTTT
TTACTTCAAGCGGATAGTTCGGCAAGTTTGTTAGCAACTATTTACAGTCGATGCCAAGTGTGGAATCTTT
CCGTGCCTAATGAAGAAATTGCTTTTGAATGGTTAAAATCAAAAAGTGCGGTAGAAAATCAGGAAATTTT
GACCGCACTTGCGATGAATCTTGGGCGTCCGCTTTTAGCATTAGAAACGTTACAAGAAGGATTTATTGAA
CAGCGTAAAAACTTCTTACGTCAATTTTGGGTGTTCTATCGCCGACGTTCGCCATTGGAATTGCTTCCGT
TGTTTGATAAAGAACGCTATGTTCAGCAAGTGGATTGGATTTTGGCTTTTCTTTCTGATTGTTTAAAACA
TAAACTTGAAATTGATAGTCATCGACAAGTGGCTGATCTTGGCCGTGGTATCGAACAATTCAGCGACGAG
CAAACTGCCCTTGGTTTATTACAAGCCATTAAAATTATGCAAAAAGTGCGGTCAGATTTGCTTACAATTA
ATGGTGTGAATGTTGAATTAATGCTATTGGATGGCTTGACACGATTAGTCACAGAAGTATTTGAAACGCA
ATAA

SEQ ID NO:12

Fig. 5A

```
>HI0456
ATGAAAGGAAAGTTTATTGTCATTGAGGGCTTAGAAGGTGCGGGGAAAAGCTCCGCTCATCAGTCTGTAG
TGCGAGTTTTGCATGAACTTGGTATTCAAGATGTTGTGTTTACGCGCGAGCCTGGTGGAACGCCACTGGC
TGAGAAATTACGTCATCTCATCAAACATGAAACCGAAGAACCCGTGACAGATAAAGCAGAGTTATTAATG
CTTTATGCGGCTCGTATTCAGTTGGTGGAAAATGTGATTAAACCTGCTTTAATGCAAGGGAAATGGGTAG
TGGGCGATCGTCACGATATGTCATCTCAGGCGTATCAGGGTGGTGGACGTCAATTAGACCCGCATTTTAT
GCTCACCTTGAAAGAAACCGTATTAGGTAATTTTGAGCCAGATCTCACAATTTATTTGGATATAGATCCG
AGCGTCGGTTTAGCGCGAGCTCGTGGACGTGGCGAGTTAGATCGTATTGAGCAAATGGATTTAGATTTTT
TCCATCGTACTCGAGCACGCTATTTAGAATTAGTAAAAGATAATCCCAAAGCAGTGGTGATTAATGCAGA
GCAGAGTATTGAACTTGTTCAAGCTGATATTGAAAGTGCGGTAAAAAATTGGTGGAAATCAAACGAAAAA
TGA
```

SEQ ID NO:13

Fig. 5B

>HI0458
ATGAAAATGAAAAAATTTGTTTTAAGATCTTTTTTATTGGCTACTTTAGGTTGTGTTGCTTTTACTTCTA
TGGCACAAGCGGAGGAACGTGTCGTAGCAACAGTGGATGGTATTCCTGTTTTAGAAAGTCAAGTGCGTGC
CAATATGGGTAAAAAAGGTGATCGCCAAAGTGCGATTGATAAAATTATTGATGATATTTTGGTGCAAAAA
GCAGTTCAAGAATCGGGAGTCAAAATTGATCCGCGTGAAATTGATCATATTGTGGAAGATACCGCAGCTA
GAAATGGTTTAACTTATGGTCAATTTTTGGATGCGTTAGATTATCAAGGCATTTCATTAAATACATTCCG
TCAGCAAATTGCCAATCAAATGGTGATGGGGGCTGTACGTAACAAAGCTATTCAAGAAAGCATTGATGTA
ACGCGTGAAGAAGTTGTCGCACTTGGTCAAAAAATGTTGGATGAGGCAAAATCACAAGGCACTGCACAAA
AAGTTACAGGTAAAGAATACGAAGTGCGTCACATTTTGTTAAAACTTAATCCATTGTTAAATGATGCTCA
AGCAAAAAAACAATTAGCTAAAATTCGTTCTGATATTATTGCAGGTAAAACAACTTTCGCTGATGCCGCA
TTAAAATATTCTAAAGATTATTTATCGGGTGCGAATGGCGGTAGTTTAGGTTATGCGTTCCCAGAAACTT
ATGCACCACAGTTTGCACAAACCGTCGTGAAAAGTAAACAAGGTGTGATTTCTGCACCATTTAAAACTGA
GTTTGGTTGGCATATTTTGGAAGTAACTGGCGTACGTGATGGCGATCTTACAGCAGAAGCCTACACACAA
AAAGCATATGAACGTTTAGTAAATACTCAATTACAAGATGCGACGAACGATTGGGTTAAAGCATTGCGTA
AAAGAGCGAATATTCAGTATTTTAATAAATAACAAATTCATCGCTACGAAATCCGTGTGATAGCATATAT
TGCCAAATTTTTTGTTTCATTTTAG

SEQ ID NO:14

Fig. 5C

>HI0599
ATGCAGGAAAAGAACTTTTCGGAAGAAGAAATTGATGATGCATTATCTCGATGCCAAGCAAAAAATTGGC
AAAGTGATCGTCGTTTTTCAGAAAATTATCTAAATTCACGCGTGCAAAAAGGTTATGGTGTAGGAAGAAT
TCGACAAGAATTACGCCAATTAAAAGGTGTGTCTTCTGATATTATTGATGAAGTTTTAATGGAATCAGAA
ATTGATTGGTATGAAATGGCTGAGAACTTGTTACGTAAAAAATTCCCAAATTATAACGAACAGCAAACGC
CTAAAATGAAACAAAAAATTTGGCAATATATGCTATCACACGGATTTCGTAGCGATGAATTTGCTGATTT
AATTGGGCAAAACCAAAGTGAATGGGATTAA

SEQ ID NO:15

Fig. 5D

>HI0887
ATGGCAGATCGTCCAATTCGTCAGGCTTTACTGAGTGTGTCTGATAAAACGGGTATTGTAGAGTTTGCTC
AAGGTTTAGTTAAACGTGGTGTAAAACTACTTTCAACAGGTGGAACGGCAAAACTTTTAGCACAAAATGC
TTTACCTGTAATAGAAGTGTCTGATTACACAGGTTTCCCAGAAATGATGGACGGTCGAGTGAAAACCTTA
CATCCCAAAGTACATGGCGGTATTCTTGGTCGTCGTGGTACAGATGATGCCATCATGCAGCAACATGGCA
TTGAAGGCATTGATATGGTCGTTGTGAATTTATATCCCTTTGCTGCCACTGTGGCAAAACCTGATTGCAC
TTTGGCTGATGCGGTAGAAAATATCGATATTGGGGGCCTACAATGGTGCGTTCTGCAGCGAAAAACCAC
AAAGATGTAGCGATCGTGGTTAATAATCATGATTTCAACGCAATTCTAGCCGAAATGGATCAACATCAAA
ACAGCCTAACTTTTGAAACTCGTTTTGACCTTGCGATTAAAGCATTTGAACATACCGCTCAATATGATTC
TATGATTGCCAACTATTTCGGTCAGCTAGTAAAACCTTATCATATTGCAGAGGAAGAAGAGGCGAATGCG
AAGTGCGGTCAATTCCCACGGACTTTAAACCTTAACTTCGTGCGTAAACAAGCTATGCGTTACGGCGAAA
ACTCCCATCAAAATGCGGCATTTTATGTTGATTTAAATGTGAAAGAAGCGAGCGTGGCTACAGCTAATCA
ACTGCAAGGTAAAGCCTTGTCTTACAATAATATTGCCGACACTGATGCAGCACTTGAATGCGTGAAAGAA
TTTGACGATCCAGCTTGCGTAATCGTTAAACATGCCAATCCATGTGGTGTGGCGTTAGGTAAGGATATTT
TAGACGCTTATAATCGCGCTTACCAAACCGATCCAACGTCTGCTTTTGGCGGCATTATTGCTTTTAACCG
TGAATTAGACGAAAAAACGGCGAATGAAATTGTGGAACGCCAATTCGTTGAAGTGATTATCGCACCGAAA
GTTTCTGCTGAAGCGCAAGAAGTAATGAAGCGTAAGAAAAATGTGCGTTTGCTTGAATGTGGTGAATGGA
CTTCTCGTTCCGAACGTTTGGATTTCAAACGTGTAAACGGCGGTTTATTAGTACAAGATGCGGATTTAGG
TATGGTTGGCGTGGATGATTTAAAAGTCGTGAGTAAACGTCAGCCAACTGAACAAGAATTAAAAGACTTA
TTATTCTGCTGGAAAGTGGCAAAATTTGTGAAATCGAATGCCATTGTTTACGCCAAAGACAATCAAACTA
TCGGCATTGGTGCAGGTCAAATGAGCCGCGTATATTCTGCGAAGATTGCGGGTATTAAAGCGCAAGATGA
AGGTTTAGAAGTGGCTGGTTGTGTGATGGCATCTGATGCGTTCTTCCCATTCCGTGACGGCATTGATGCG
GCGGCGAAAGTGGGTATTCAATGTGTGATCCATCCAGGTGGATCAATGCGCGATCAAGAAGTCATTGATG
CGGCGGATGAACATAATATGGTAATGGTATTGACTGGAATGCGACATTTTAGACATTAA

SEQ ID NO:16

Fig. 5E

```
>HI0904
ATGAATTCAAATTATTTACTTCTTCCCCACTTTGATCCGAGTATTTTTACGCTTGGCGATAGTAATATCG
GCTTACGTTGGTATGGCTTGATGTACCTTTTAGGTTTTGTTTTTGCACGTTGGCTTGCGGTTCGCCGTGC
TAATCGCCCAAATAGCGGTTGGACAGTAGATCAAGTTGATAGCTTACTTTTCAACGGTTTTATGGGGGTG
TTTATTGGCGGACGTGTTGGCGATGTATTTTTCTATAATCTCGATCATTTCTTACAAGAACCACTTTATT
TATTCCGCGTTTGGGAAGGTGGAATGTCGTTCCACGGTGGCTTAATTGGTGTAATTGTTGCTATGATTTG
GACATCTTATTCTCAAAAACGTAATTTTTGGCAAACGGCTGATTTTGTTGCGCCTTTGATTCCGTTTGGT
TTAGGTTTAGGCAGAATTGGTAATTTCATTAATCTTGAACTATGGGGACGCGAAACGAATGTGCCTTGGG
CAATGATTTTCCCGAATGATCCTCTTTTACTGCCTCGTCATCCATCACAACTTTATGAAGCCTTTTTAGA
AGGCCTGGTGTTGTTTACGATTCTGAATATTTTTATTAAAAAACCACGTCCAATGGCTTCTGTTGCAGGT
TTATTCTTAATTGGTTATGGCGTCTTCCGTTTTATTGTGGAATATGTGCGTGAACCTGAAGTTGAAAATT
TCTTTGGGATTATTACACGAGGGCAAGCCCTTTGCTTGCCGATGATTATTGGTGGTGCTTTCATTATGGC
TTGGGCTTATTCACGCAAAAGTGCGGTCATAAAATAG
```

SEQ ID NO:17

Fig. 5F

>HI0906
ATGGATGCAGCAAAAGTGCGGTCAGAATTTGACGAGAAAATGATGCGCTACGCCCTTGAGCTTGCCGATA
AAGCGGAAGCGTTAGGTGAGATTCCTGTGGGGGCGGTGCTGGTGGATGACGCTAGAAATATTATTGGAGA
AGGTTGGAATCTCTCCATTGTTCAAAGTGATCCTACTGCACATGCTGAAATTATCGCTTTGCGTAATGGT
GCGAAAAATATTCAAAATTATCGCCTACTGAATAGCACGCTTTATGTGACATTAGAGCCTTGCACAATGT
GCGCAGGGGCAATTTTGCATAGCCGTATTAAACGTCTTGTGTTCGGTGCATCTGATTATAAAACTGGCGC
GATTGGATCACGTTTTCATTTTTTTGATGATTACAAGATGAATCATACTTTAGAGGTTACATCTGGCGTA
TTGGCAGAAGAGTGTAGTCAAAAATTGAGTACATTTTTTCAGAAAAGACGCGAGGAGAAAAAAATAGAGA
AAGCATTATTAAAAAGTCTGAGTGATAAGTAA

SEQ ID NO:18

Fig. 5G

>HI0907
ATGGAAAACAAGGCTGAGCGTTATCAAAAAGCAGTCAATATTACGGATGTGCTTGAGCAATCGCCCTTTG
CCAAAATAATCAAAAAAGGTCTTGCTATCAATGAAATCAATCAAAAATTTAACCGCATTTTTCCACAGGA
ATTTCACGGCAAATTTCGTATTGGTAATATGACAGATAACTCAATTTTTATTGAGACAGCAAATGCGATC
GTTCGCCAAGGAATTTTATTCAGACAGACAGAATTGTTGAAACTCATTCAAGAAGAGTTTCCGCAAGTAA
CAGGATTTGAGATAACGATCAATCCTGGATTTTAA

SEQ ID NO:19

Fig. 5H

>HI0908
ATGATTTCAGGCACTGTCAAACCGAATTTTTGGTCGCGATTACTTTTAAGTATCATCGCAATTTTTGCTT
TGCCTAACGCACAAAGTTTTGAAAATCAAAATAATACGGAAAATTATTCCTCAAGTGTTTCCATTCAACA
AGCGTTAGAAACGGTAAAAGTTGCTCGTGAAGTGCAACGACAAGCCATTCCTCAACCTTCAATTTCCCGT
CAAACTGAAAAACAACTTAAAATTCAACCGCACTTTTTTACTGAAGCGTTGAATATTAGCGCGCCAATTC
GAGCAGGCCCCTTGCTTATTTAA

SEQ ID NO: 20

Fig. 5I

>HI0909
ATGAGCATTTTAACAAGAATTTTTGGTAGTCGTAATGAACGCGTTTTACGTAAATTAAAAAAACAAGTCG
TAAAAATTAATAAAATGGAGCCTGCTTTTGAGGCATTAAGTGATGATGAATTAAAAGCAAAAACACAAGA
GTTTCGTGATCGTTTAAGTGGTGGCGAAACTTTGCAACAAATTTTACCAGAAGCATTCGCAACGGTACGC
GAAGCAAGTAAGCGTGTGCTTGGTATGCGCCATTTTGATGTTCAGCTTATCGGTGGGATGGTATTGACTA
ACCGCTGTATCGCAGAAATGCGTACTGGTGAAGGTAAAACATTAACGGCGACTTTGCCTTGTTATTTAAT
CGCACTTGAAGGTAAAGGCGTTCACGTGGTAACCGTGAATGATTATCTTGCTCGCCGAGATGCAGAAACA
AACCGTCCGTTATTTGAATTTTTAGGCATGAGTGTAGGCGTCAATATTCCTGGTTTATCGCCAGAAGAAA
AACGTGCAGCTTATGCGGCAGATATTACTTATGCAACCAATAGTGAACTTGGTTTTGATTATTTACGTGA
CAACTTAGCCCACTCAAAAGAAGAGCGTTTCCAACGTACTTTAGGCTATGCGTTGGTGGATGAAGTGGAT
TCTATCTTAATCGATGAAGCGCGTACGCCATTGATTATTTCTGGTCAGGCAGAAAACAGTTCAGAGCTTT
ATATTGCGGTAAATAAATTGATCCCAAGTTTAATTAAACAAGAAAAAGAAGATACGGAAGAATATCAAGG
AGAGGGCGATTTCACTTTAGATTTGAAATCTAAACAAGCGCATTTAACCGAACGTGGTCAAGAAAAAGTA
GAAGATTGGTTAATTGCACAAGGTTTAATGCCTGAGGGGGACTCTTTGTATTCTCCTAGTCGAATTGTAT
TGCTTCATCACGTTATGGCTGCATTGCGTGCGCACACATTGTTTGAAAAAGATGTCGATTACATTGTGAA
GGACGGTGAAATCGTGATTGTTGATGAACACACTGGTCGTACAATGGCGGGGCGTCGTTGGTCAGATGGT
TTGCACCAAGCCATTGAGGCAAAAGAAGGGGTGGATGTTAAGAGCGAAAACCAAACTGTTGCATCAATTT
CTTACCAAAACTACTTCCGTTTATATGAACGTCTTGCGGGTATGACGGGGACTGCGGATACCGAAGCATT
TGAGTTCCAACAAATTTATGGCTTGGAAACTGTTGTAATTCCAACAAATCGTCCAATGATTCGTGATGAT
CGCACTGATGTGATGTTTGAAAATGAACAATATAAATTTAATGCGATTATTGAAGACATTAAAGATTGTG
TAGAACGCCAGCAACCAGTATTAGTGGGGACGATTTCAGTCGAAAAATCAGAAGAATTATCTAAAGCGTT
AGATAAAGCAGGTATAAAACACAATGTGTTGAATGCGAAATTCCACCAACAAGAAGCGGAAATCGTGGCA
GAAGCAGGATTTCCTAGCGCAGTGACTATCGCAACGAATATGGCGGGTCGAGGTACGGATATTATTCTTG
GCGGTAACTGGAAAGCGCAGGCTGCCAAATTAGAAAATCCAACTCAAGAACAAATTGAAGCCCTTAAAGC

SEQ ID NO:21

AGAGTGGGAGAAAAACCACGAAATTGTAATGAAAGCGGGTGGGTTGCATATTATCGGTACAGAGCGTCAC
GAATCTCGCCGTATTGATAACCAGTTGCGCGGTCGTTCTGGGCGTCAAGGTGACCCCGGTTCTTCTCGTT
TCTATCTTTCTTTGGAAGATGGTTTAATGCGCATTTATTTGAATGAGGGTAAGCTCAATTTAATGCGTAA
AGCGTTCACGGTAGCAGGCGAGGCAATGGAGTCGAAAATGTTGGCGAAAGTGATTGCATCTGCTCAAGCA
AAAGTTGAGGCGTTCCATTTTGATGGCCGTAAAAACCTACTTGAATATGATGATGTGGCAAATGACCAAC
GTCACGCGATTTATGAGCAACGCAATCATTTGCTTGATAATGATGATATTTCTGAAACTATCAACGCTAT
TCGCCACGATGTGTTTAATGGTGTGATTGATCAATATATTCCACCACAATCTTTGGAAGAACAATGGGAT
ATTAAAGGGCTTGAAGAACGTTTATCTCAAGAGTTTGGTATGGAATTACCGATTTCTAATTGGTTGGAAG
AAGATAATAATCTTCACGAAGAAAGTTTGCGCGAACGCATTGTGGAAATTGCAGAAAAGGAATACAAAGA
AAAAGAGGCTTTGGTTGGCGAAGACGCTATGCGCCATTTTGAAAAAGGTGTTATGTTGCAAACCTTAGAT
GAACTTTGGAAAGAACACTTAGCTTCGATGGATTATTTACGCCAAGGTATTCATTTACGTGGCTATGCCC
AAAAAGATCCAAAACAAGAGTATAAAAAAGAATCTTTCCGTATGTTTACGGAAATGTTGGATTCTTTAAA
ACACCAGGTTATCACGGCTTTAACCCGTGTACGTGTGCGTACTCAAGAAGAAATGGAAGAAGCTGAACGT
GCTCGTCAAGAAATGGCAGCACGTATCAATCAAAATAATTTACCTGTGGATGAAAATAGTCAGACAACTC
AAAATTCAGAGACTGAAGATTATTCAGATCGTCGCATTGGTCGCAACGAGCCTTGTCCTTGTGGGTCGGG
TAAAAAATATAAGCATTGTCACGGCAGTCGTGTGGCACGCCAGTAA

SEQ ID NO:21

>HI1650
ATGCCAAACGAACGTAATATTCAAAATTATCACTCGACTTACAACAACATTCGGGATTGGCTTGGTTATC
AAAAAGCTGGCGAGGAAAAAGCAAAGTCGACCATCAATTAG

SEQ ID NO:22

Fig. 5K

>HI1651
ATGGATGGCATATTACGTAAACTCATTTCAATTAAGGATTTACACCATTGCCTGCAGAAATTTTTTGTGG
ATGAAAGAGAATCTATTATAGAAATGAATGATAATAAGCTTTCAGAACAGTTTGATTTAGCATTGATTGA
AACGCATGGTAAATCAAAAATTTTAAAAAATTTATCTTTATTCAAACAAACCATGTCTAATTATCTTACT
CAATTATCAAAAGATAATATGAAAGAAACAGAAAATACTGTTCATAAAATTAAAAGAGTAGCAGCATAG

SEQ ID NO:23

Fig. 5L

>HI1654
ATGACTGATTTAACCGGAATTTTATACATTGTTGCCACGCCCATTGGCAATTTACAAGATATTACCCAAC
GTGCTTTAGAGACTTTTGCTCAAGTGGATTTAATTGCAGCAGAAGATACTCGCCATAGTGGACTTTTATT
GAGCCATTACGGCATTAAGAAGCCATTTTTTGCTTTGCACGATCATAACGAACAAGAAAAAGCGCATATT
TTGGTGGAAAAGCTCAAGCAGGGGAGTAATATTGCCTTGATTTCTGATGCGGGGACGCCATTAATCAGTG
ACCCTGGTTTTCATTTAGTACGCCAATGCCGTGAAGCTGGCATTCGAGTTGTGCCTTTGCCAGGAGCTTG
TGCGGCAATTACCGCTCTTTGTGCATCGGGGATTGCTTCTGATAGATTTTGTTTTGAAGGCTTTTTACCT
GCGAAAAGTAAAGCACGCAAAGATAAATTAGAAAATATCGCAGAAGAAGACCGCACTTTGATTTTTTATG
AATCCACTCACCGTATTTTAGATACACTAGAAGATATGCAAGCGGTGCTAGGGGAAGAACGATACATTGT
GTTAGCCCGTGAAATGACTAAAACTTGGGAAACGATTACGGGGAATACGATTAAAAATTTACGCGAATGG
CTTTTAGAAGATCCCAATCGTACAAAAGGCGAGATGGTTTTGATTGTGGAAGGCAAACCAAAGTCTGACA
ATAACGATGAAATTTCGCCGCAAGCGGTAAAGGCACTTGAGTTAATTGCAGAAGAATTGCCACTTAAAAA
AGCAGCAGCTATAGTTGCTGAGTTGTATGGTTATAAGAAGAATGCTTTGTATCAATTTGGATTAGCGCAT
TTGGAAAAATAA

SEQ ID NO:24

Fig. 5M

>HI1655
ATGTCTATTCTATTACAAGGCGAACGTTTTAAAAAACGTTTAATGCCAATTTTATTGTCAATGGCTTTAG
CTGGCTGTTCAAATCTACTTGGTAGCAATTTCACGCAAACCTTACAAAAAGATGCAAATGCAAGTTCTGA
ATTTTATATAAACAAATTAGGGCAAACACAAGAACTTGAAGATCAACAAACCTATAAATTGCTCGCGGCT
CGAGTGTTAATCCGTGAAAATAAGGTTGAACAATCGGCAGCGTTATTGAGGGAATTAGGCGAATTAAATG
ATGCGCAAAAATTAGATCGTGCATTAATTGAAGCGAGAATTTCTGCTGCAAAAAATGCCAATGAAGTCGC
ACAAAATCAATTACGTGCATTGGATTTAAATAAACTAAGCCCGTCACAAAAATCTCGTTATTACGAAACC
TTAGCTATTGTTGCCGAAAACCGTAAAGACATGATTGAAGCGGTAAAAGCGCGGATAGAAATGGATAAGA
ATTTAACAGATGTACAACGTCATCAAGATAATATTGATAAAACTTGGGCTTTATTGCGTTCAGCGAATAC
TGGCGTTATTAATAATGCCTCTGATGAAGGTAATGCAGCTTTAGGCGGTTGGCTAACATTAATCAAAGCC
TACAACGATTATATTCGTCAGCCTGTACAATTAAGCCAAGCCTTACAAAGTTGGAAAAATGCTTATCCAA
ATCATGCAGCCGCAACGTTGTTCCCAAAAGAATTGCTTACATTGCTTAATTTCCAACAAACGAATGTGTC
ACAAATTGGTTTACTCTTGCCATTAAGTGGTGACGGACAAATTCTTGGCACAACCATTCAATCGGGTTTT
AACGACGCGAAAGGTAACTCAACCATTCCAGTGCAAGTGTTTGATACCTCAATGAATTCTGTCCAAGATA
TCATTGCGCAAGCAAAACAAGCGGGGATTAAAACCTTAGTTGGCCCATTACTAAAACAAAATCTTGATGT
GATTTTAGCAGATCCTGCTCAAATTCAAGGTATGGATGTGCTTGCATTAAATGCCACACCAAATTCTCGT
GCGATTCCTCAACTTTGTTATTACGGACTTTCGCCAGAAGATGAAGCTGAATCTGCCGCCAATAAAATGT
GGAACGATGGCGTGCGTAATCCACTTGTCGCAATGCCGCAAAATGATTTAGGACAACGCGTAGGCAATGC
CTTTAATGTACGTTGGCAACAATTAGCAGGTACTGATGCGAATATCCGTTACTACAATTTGCCTGCGGAT
GTGACCTATTTCGTTCAAGAAAATAACTCAAATACAACCGCACTTTATGCCGTAGCAAGTCCAACTGAAC
TGGCAGAAATGAAAGGTTATTTAACAAATATCGTACCTAATTTAGCGATTTATGCCAGTTCTCGAGCAAG
CGCAAGTGCGACAAACACTAATACCGACTTCATCGCACAGATGAACGGTGTACAGTTTAGTGATATTCCA
TTTTTTAAAGATACCAATTCTCCACAATATCAGAAGTTAGCAAAATCCACGGGGGGCGAATATCAATTGA
TGCGTTTATATGCAATGGGTGCGGATGCGTGGTTGCTCATTAATCAATTTAATGAATTACGCCAAGTGCC
AGGCTATCGCTTGAGTGGCTTAACAGGGATTTTAAGTGCTGATACCAACTGTAATGTTGAACGCGATATG
ACTTGGTATCAATATCAAGATGGTGCAATTGTACCAGTTGCAAACTAA

SEQ ID NO:25

Fig. 5N

TCATGGCAAATCATTTCCGTACAGATCGTGTGGGCATGGAAATCAAGCGT
GAAGTCAATGAGATTTTGCAAAAGAAAGTCCGTGATCCACGTGTCCAAGG
TGTGACCATCATAGATGTTCAGATGCTGGGTGACTTGTCTGTTGCCAAGG
TTTATTACACCATTTTGAGTAACCTTGCTTCGGATAACCAAAAAGCCCAA
ATCGGGCTTGAAAAAGCAACTGGTACCATCAAACGTGAACTTGGTCGCAA
TTTGAAATTGTACAAAATCCCAGATTTGACCTTCGTCAAAGACGAGTCCA
TCGAGTATGGAAACAAGATTGACGAGATGCTACGCAATCTGGATAAG rbfA (SEQ ID NO: 26)

Fig. 5O

GGATGTGAAAAGCCACTCATCAAGTGTGGAAGAAGCTGTCGCTGCAAAAATTGCTGCCAGCTTTAAGCCT
GCAGCTGCTCCGAAAGTAGAAGCAAAACCTGCAGCCCCAAAAGTAAGTGCAGAAAAGAAAGCCGAAAAAT
CTGAGCCAGCTAAACCAGCTGTAGCTAAGGAAGAGGCAAAACCTGCAGCCCCAAAAGCAAGTGCAGAAAA
GAAAGCCGAAAAGTCTGAACCAGTAAAACCAGCTGTAGCCAAGGAAGAGGCAAAACCAGCTGAGCCAGTC
ACTCCGAAAACAGAAAAAGTAGCGGCTAAACCGCAAAGTCGTAATTTCAAGGCTGAGCGTGAAGCACGTG
CTAAAGAGCAGGCAGAGCGACGCAAGCAAAATAAGGGCAATAACCGTGACCAACAACAAAACGGAAACCG
TCAGAAAAACGACGGCCGTAATGGTGGAAAACAAGGTCAAAGCAACCGCGACAATCGTCGCTTTAATGAC
CAAGCTAAGAAGCAGCAAGGTCAGCAAAAACGTAGAAATGAGCGCCGTCAGCAAGAGGATAAACGTTCAA
ATCAAGCGGCTCCACGTATTGACTTTAAAGCCCGTGCAGCAGCCCTAAAAGCAGAGCAAAATGCAGAGTA
CGCTCGTTCAAGTGAGGAACGCTTCAAGCAGTATCAGGCTGCTAAAGAAGCCTTGGCTCAAGCTAACAAA
CGCAAGGAACCAGAGGAAATCTTTGAAGAAGCGGCTAAGTTAGCTGAACAAGCACAGCAAGTTCAAGCAG
TGGTTGAAGTCGTCCCTGAGAAAAAAGAACCTGCAGTGGATACACGTCGTAAAAAACAAGCTCGACCAGA
CAAAAATCGTGACGATTATGATCATGAAGAAGATGGTCCTAGAAAACAACAAAAGAATCGAAGTAGTCAA
AATCAAGTGAGAAATCAAAAGAATAGTAACTGGAATAACAACAAAAAGAACAAAAAAGGCAATAACAAGA
ACAACCGTAATCAGACTCCAAAACCTGTTACGGAGCGTAAATTCCATGAATTGCCAACAGAATTTGAATA
TACAGATGGTATGACCGTTGCGGAAATCGCAAAACGTATCAAACGTGAACCAGCTGAAATTGTTAAGAAA
CTTTTCATGATGGGTGTCATGGCCACACAAAACCAATCCTTGGATGGGGAAACAATTGAACTCCTCATGG
TGGATTACGGTATCGAAGCCAAACAAAAGGTTGAAGTGGATAATGCTGACATCGAACGTTTCTTTGTCGA
AGATGGTTATCTCAATGAAGATGAATTGGTTGAGCGTCCACCAGTTGTTACTATCATGGGACACGTTGAC
CACGGTAAAACAACCCTTTTGGATACTCTTCGTAACTCACGTGTTGCGACAGGTGAAGCAGGTGGTATTA
CTCAGCATATCGGTGCCTACCAAATCGTGGAAAATGGTAAGAAGATTACCTTCCTTGATACACCAGGACA
CGCGGCCTTTACATCAATGCGTGCGCGTGGTGCTTCTGTTACCGATATTACGATCTTGGTCGTAGCGGCA
GATGACGGGGTTATGCCTCAGACTATTGAAGCCATCAACCACTCAAAAGCAGCTAACGTTCCAATCATCG
TAGCTATTAACAAGATTGATAAACCAGGTGCTAACCCAGAACGCGTTATCGGTGAATTGGCAGAGCATGG

IF-2 (SEQ ID NO: 27)

TGTGATGTCAACTGCTTGGGGTGGAGATTCTGAATTTGTTGAAATTTCGGCTAAATTCAACCAAAATATC
GAAGAATTGTTGGAAACAGTCCTTCTTGTGGCTGAAATCCAAGAACTCAAAGCAGACCCAACAGTTCGTG
CGATCGGTACGGTTATCGAAGCGCGCTTGGATAAAGGAAAAGGTGCGGTCGCAACCCTTCTTGTACAACA
AGGTACCTTGAATGTTCAAGACCCAATCGTTGTCGGAAATAcTTCGGTCGTGTCCGTGCTATGACCAACG
ACCTTGGTCGTCGTGTTAAAGTTGCTGGACCATCAACACCAGTCTCTATCACAGGTTTGAACGAAGCACC
GATGGCGGGTGACCACTTTGCCGTTTACGAGGATGAAAAATCTGCGCGTGCAGCAGGTGAAGAGCGTGCC
AAACGTGCCCTCATGAAACAACGTCAAGCTACCCAACGTGTTAGCCTTGAAAACCTCTTTGATACCCTTA
AAGCTGGGGAACTCAAATCTGTTAATGTTATCATCAAGGCTGATGTACAAGGTTCTGTTGAAGCCCTTTC
TGCCTCACTTCAAAAGATTGACGTGGAAGGTGTCAAAGTGACTATCGTCCACTCAGCGGTCGGTGCTATC
AACGAATCAGACGTGACCCTTGCCGAAGCTTCAAATGCCTTTATCGTTGGTTTCAACGTACGCCCTACAC
CACAAGCTCGTCAACAAGCAGAAGCTGACGATGTGGAAATCCGTCTTCACAGCATTATCTACAAGGTTAT
CGAAGAGATGGAAGAAGCTATGAAAGGGATGCTTGATCCAGAATTTGAAGAAAAAGTTATTGGTGAAGCG
GTTATCCGTGAAACCTTCAAGGTGTCTAAAGTGGGAACTATCGGTGGATTTATGGTTATCAACGGTAAGG
TTGCCCGTGACTCTAAAGTCCGTGTTATCCGTGATGGTGTCGTTATCTATGATGGTGAACTCGCAAGCTT
GAAACACTATAAAGACGACGTGAAAGAAGTGACAAACGGTCGTGAAGGTGGATTGATGATCGACGGCTAC
AATGATATTAAGATGGATGATGTGATTGAGGCGTATGTCATGGAAGAAATCAAGAGA

IF-2 (SEQ ID NO: 27)

AATAAGCAAAAGATAAGTAATCTCTTGGGGCTTGCTCAGCGAGCAGGGCG
CATCATATCGGGTGAAGAATTGGTGGTCAAGGCCATTCAAGACGGCAAGG
CCAAGTTGGTCTTTCTAGCTCATGATGCTGGACCCAATCTGACCAAGAAG
ATTCAAGATAAAAGTCATTATTATCAAGTAGAAATTGTAACCGTGTTTTC
AACACTGGAATTAAGCATAGCAGTCGGGAAATCGAGAAAGGTTTTGGCTG
TAACAGATGCTGGATTTACAAAGAAAATGAGGTCTCTTATGGAA

L7AE (SEQ ID NO: 28)

Fig. 5Q

ATGAGTAAAGAAATGCTAGAGGCCTTCCGCATTTTGGAAGAAGACAAGGG
AATCAAAAAAGAAGATATCATCGACGCAGTAGTAGAGTCGCTTCGTTCCG
CTTATCGCAGACGCTATGGTCAGTCAGACAGCGTAGCTATTGACTTCAAC
GAAAAAACAGGTGACTTTACAGTTTATACTGTCCGTGAAGTTGTTGATGA
AGTATTTGATAGCCGTTTGGAAATCAGCTTGAAAGATGCTCTTGCCATTA
ATTCAGCTTATGAACTTGGAGACAAAATCAAGTTTGAAGAAGCACCAGCT
GAGTTTGGTCGTGTAGCAGCCCAATCTGCCAAACAAACCATCATGGAAAA
AATGCGCAaCAAACACGTGCCATCACTTACAATACTTACAAAGAACATGA
GCAAGAAATCATGTCTGGTACAGTAGAACGCTTTGACAACCGCTTTATCT
ATGTCAACCTTGGTAGCATCGAAGCCCAATTGTCAAAACAAGACCAAATT
CCTGGAGAAGTTTTTGCTTCTCATGATCGTATCGAAGTTTATGTTTACAA
GGTTGAAGACAACCCTCGTGGTGTGAACGTCTTTGTTAGCCGTAGTCATC
CAGAAATGATCAAACGTTTAATGGAGCAAGAAATTCCAGAAGTTTATGAT
GGAACTGTTGAAATCATGAGCGTGGCTCGTGAAGCAGGTGACCGTACGAA
GGTTGCTGTTCGTAGCCACAATCCAAACGTGGATGCTATCGGTACAATCG
TTGGACGTGGTGGTGCTAATATCAAGAAGATTACTAGCAAATTCCACCCA
GCTCGTTACGATGCTAAAAATGACCGCATGGTACCAATCGAAGAAAATAT
CGATGTTATCGAGTGGGTAGCAGATCCAGCTGAATTTATCTACAATGCCA
TCGCTCCTGCTGAGGTTGACCAAGTTATCTTTGATGAAAACGACAGCAAA
CGTGCCTTGGTGGTTGTTCCAGATAACAAGCTTTCTCTTGCCATTGGTCG
TCGTGGACAAAACGTGCGCTTGGCGGCTCACTTGACTGGTTACCGTATCG
ATATCAAGTCTGCTAGCGAA nusA (SEQ ID NO: 29)

Fig. 5R

SEQUENCE LISTING

```
<160> NUMBER OF SEQ ID NOS: 29

<210> SEQ ID NO 1
<211> LENGTH: 24
<212> TYPE: DNA
<213> ORGANISM: Artificial Sequence
<220> FEATURE:
<223> OTHER INFORMATION: Synthetic based on Streptococcus pneumoniae

<400> SEQUENCE: 1

ctttctgtaa aatgtgggat tcaa                                          24


<210> SEQ ID NO 2
<211> LENGTH: 24
<212> TYPE: DNA
<213> ORGANISM: Artificial Sequence
<220> FEATURE:
<223> OTHER INFORMATION: Synthetic based on Streptococcus pneumoniae

<400> SEQUENCE: 2

aattattatg gagtcgtcgt ttgg                                          24
```

-continued

<210> SEQ ID NO 3
<211> LENGTH: 21
<212> TYPE: DNA
<213> ORGANISM: Artificial Sequence
<220> FEATURE:
<223> OTHER INFORMATION: Synthetic based on Haemophilus influenzae

<400> SEQUENCE: 3
ccggggactt atcagccaac c 21

<210> SEQ ID NO 4
<211> LENGTH: 25
<212> TYPE: DNA
<213> ORGANISM: Artificial Sequence
<220> FEATURE:
<223> OTHER INFORMATION: Synthetic based on Haemophilus influenzae

<400> SEQUENCE: 4 cgccttttg taaatcacgc atcgc 25

<210> SEQ ID NO 5
<211> LENGTH: 25
<212> TYPE: DNA
<213> ORGANISM: Artificial Sequence
<220> FEATURE:
<223> OTHER INFORMATION: Synthetic based on Haemophilus influenzae

<400> SEQUENCE: 5
gcggatgaaa caaatcgacc agcag 25

<210> SEQ ID NO 6
<211> LENGTH: 21
<212> TYPE: DNA
<213> ORGANISM: Artificial Sequence
<220> FEATURE:
<223> OTHER INFORMATION: Synthetic based on Haemophilus influenzae

<400> SEQUENCE: 6
tcacgccgct gattttgctg g 21

<210> SEQ ID NO 7
<211> LENGTH: 25
<212> TYPE: DNA
<213> ORGANISM: Artificial Sequence
<220> FEATURE:
<223> OTHER INFORMATION: Synthetic based on Haemophilus influenzae

<400> SEQUENCE: 7
gggagcaaga aaagcgacag aagcc 25

<210> SEQ ID NO 8
<211> LENGTH: 20
<212> TYPE: DNA
<213> ORGANISM: Artificial Sequence
<220> FEATURE:
<223> OTHER INFORMATION: Synthetic based on Haemophilus influenzae

<400> SEQUENCE: 8
aaatcatcca tcgtgaccca 20

<210> SEQ ID NO 9
<211> LENGTH: 25
<212> TYPE: DNA
<213> ORGANISM: Artificial Sequence
<220> FEATURE:
<223> OTHER INFORMATION: Synthetic based on Haemophilus influenzae -continued

<400> SEQUENCE: 9
cccgaataaa ttgcttatcg cctcg 25

<210> SEQ ID NO 10
<211> LENGTH: 25
<212> TYPE: DNA
<213> ORGANISM: Artificial Sequence
<220> FEATURE:
<223> OTHER INFORMATION: Synthetic based on Haemophilus influenzae

<400> SEQUENCE: 10
gggagcaaga aaagcgacag aagcc 25

<210> SEQ ID NO 11
<211> LENGTH: 23
<212> TYPE: DNA
<213> ORGANISM: Artificial Sequence
<220> FEATURE:
<223> OTHER INFORMATION: Synthetic based on Haemophilus influenzae

<400> SEQUENCE: 11
caggcgtatc agggtggtgg acg 23

<210> SEQ ID NO 12
<211> LENGTH: 984
<212> TYPE: DNA
<213> ORGANISM: Haemophilus influenzae

<400> SEQUENCE: 12
atgaccgcac tttacccttg gctaatgcca atttatcatc aaattgctca aacctttgac 60
gaagggttgg ggcatcatgc tgtgctgatt aaagctgatt ctggtttagg cgtagagagt 120
ttatttaatg cacttgcaca gaaaataatg tgtgtagctc aaggcgataa accttgtggt 180
caatgccatt cttgtcattt aatgcaagcc catagccatc cagattatca cgaattaagc 240
cccattaacg gtaaggatat tggcgttgat caagtacgcg acattaatga aatggttgcg 300
cagcacgcac aacaaaacgg caataaagtg gtgtatgtgc aaggggcgga acgtttaacg 360
gaagcggctg ctaatgcatt attgaaaaca ttggaagagc ctcgtccaaa tacttatttt 420
ttacttcaag cggatagttc ggcaagtttg ttagcaacta tttacagtcg atgccaagtg 480
tggaatcttt ccgtgcctaa tgaagaaatt gcttttgaat ggttaaaatc aaaaagtgcg 540
gtagaaaatc aggaaatttt gaccgcactt gcgatgaatc ttgggcgtcc gcttttagca 600
ttagaaacgt tacaagaagg atttattgaa cagcgtaaaa acttcttacg tcaattttgg 660
gtgttctatc gccgacgttc gccattggaa ttgcttccgt tgtttgataa agaacgctat 720
gttcagcaag tggattggat tttggctttt ctttctgatt gtttaaaaca taaacttgaa 780
attgatagtc atcgacaagt ggctgatctt ggccgtggta tcgaacaatt cagcgacgag 840
caaactgccc ttggtttatt acaagccatt aaaattatgc aaaaagtgcg gtcagatttg 900
cttacaatta atggtgtgaa tgttgaatta atgctattgg atggcttgac acgattagtc 960
acagaagtat ttgaaacgca ataa 984

<210> SEQ ID NO 13
<211> LENGTH: 633
<212> TYPE: DNA
<213> ORGANISM: Haemophilus influenzae

<400> SEQUENCE: 13

-continued

```
atgaaaggaa agtttattgt cattgagggc ttagaaggtg cggggaaaag ctccgctcat     60
cagtctgtag tgcgagtttt gcatgaactt ggtattcaag atgttgtgtt tacgcgcgag    120
cctggtggaa cgccactggc tgagaaatta cgtcatctca tcaaacatga aaccgaagaa    180
cccgtgacag ataaagcaga gttattaatg ctttatgcgg ctcgtattca gttggtggaa    240
aatgtgatta aacctgcttt aatgcaaggg aaatgggtag tgggcgatcg tcacgatatg    300
tcatctcagg cgtatcaggg tggtggacgt caattagacc cgcattttat gctcaccttg    360
aaagaaaccg tattaggtaa ttttgagcca gatctcacaa tttatttgga tatagatccg    420
agcgtcggtt tagcgcgagc tcgtggacgt ggcgagttag atcgtattga gcaaatggat    480
ttagattttt tccatcgtac tcgagcacgc tatttagaat tagtaaaaga taatcccaaa    540
gcagtggtga ttaatgcaga gcagagtatt gaacttgttc aagctgatat tgaaagtgcg    600
gtaaaaaatt ggtggaaatc aaacgaaaaa tga                                 633
```

<210> SEQ ID NO 14
<211> LENGTH: 1005
<212> TYPE: DNA
<213> ORGANISM: Haemophilus influenzae

<400> SEQUENCE: 14

```
atgaaaatga aaaaatttgt tttaagatct tttttattgg ctactttagg ttgtgttgct     60
tttacttcta tggcacaagc ggaggaacgt gtcgtagcaa cagtggatgg tattcctgtt    120
ttagaaagtc aagtgcgtgc caatatgggt aaaaaaggtg atcgccaaag tgcgattgat    180
aaaattattg atgatatttt ggtgcaaaaa gcagttcaag aatcgggagt caaaattgat    240
ccgcgtgaaa ttgatcatat tgtggaagat accgcagcta gaaatggttt aacttatggt    300
caatttttgg atgcgttaga ttatcaaggc atttcattaa atacattccg tcagcaaatt    360
gccaatcaaa tggtgatggg ggctgtacgt aacaaagcta ttcaagaaag cattgatgta    420
acgcgtgaag aagttgtcgc acttggtcaa aaaatgttgg atgaggcaaa atcacaaggc    480
actgcacaaa aagttacagg taaagaatac gaagtgcgtc acattttgtt aaaacttaat    540
ccattgttaa atgatgctca agcaaaaaaa caattagcta aaattcgttc tgatattatt    600
gcaggtaaaa caactttcgc tgatgccgca ttaaaatatt ctaaagatta tttatcgggt    660
gcgaatggcg gtagtttagg ttatgcgttc ccagaaactt atgcaccaca gtttgcacaa    720
accgtcgtga aaagtaaaca aggtgtgatt tctgcaccat ttaaaactga gtttggttgg    780
catattttgg aagtaactgg cgtacgtgat ggcgatctta cagcagaagc ctacacacaa    840
aaagcatatg aacgtttagt aaatactcaa ttacaagatg cgacgaacga ttgggttaaa    900
gcattgcgta aaagagcgaa tattcagtat tttaataaat aacaaattca tcgctacgaa    960
atccgtgtga tagcatatat tgccaaattt tttgtttcat tttag                   1005
```

<210> SEQ ID NO 15
<211> LENGTH: 381
<212> TYPE: DNA
<213> ORGANISM: Haemophilus influenzae

<400> SEQUENCE: 15

```
atgcaggaaa agaacttttc ggaagaagaa attgatgatg cattatctcg atgccaagca     60
aaaaattggc aaagtgatcg tcgtttttca gaaaattatc taaattcacg cgtgcaaaaa    120
ggttatggtg taggaagaat tcgacaagaa ttacgccaat taaaaggtgt gtcttctgat    180
attattgatg aagttttaat ggaatcagaa attgattggt atgaaatggc tgagaacttg    240
```

-continued

```
ttacgtaaaa aattcccaaa ttataacgaa cagcaaacgc ctaaaatgaa acaaaaaatt    300

tggcaatata tgctatcaca cggatttcgt agcgatgaat ttgctgattt aattgggcaa    360

aaccaaagtg aatgggatta a                                              381
```

<210> SEQ ID NO 16
<211> LENGTH: 1599
<212> TYPE: DNA
<213> ORGANISM: Haemophilus influenzae

<400> SEQUENCE: 16

```
atggcagatc gtccaattcg tcaggcttta ctgagtgtgt ctgataaaac gggtattgta     60

gagtttgctc aaggtttagt taaacgtggt gtaaaactac tttcaacagg tggaacggca    120

aaacttttag cacaaaatgc tttacctgta atagaagtgt ctgattacac aggtttccca    180

gaaatgatgg acggtcgagt gaaaacctta catcccaaag tacatggcgg tattcttggt    240

cgtcgtggta cagatgatgc catcatgcag caacatggca ttgaaggcat tgatatggtc    300

gttgtgaatt tatatccctt tgctgccact gtggcaaaac ctgattgcac tttggctgat    360

gcggtagaaa atatcgatat tggggggcct acaatggtgc gttctgcagc gaaaaaccac    420

aaagatgtag cgatcgtggt taataatcat gatttcaacg caattctagc cgaaatggat    480

caacatcaaa acagcctaac ttttgaaact cgttttgacc ttgcgattaa agcatttgaa    540

cataccgctc aatatgattc tatgattgcc aactatttcg gtcagctagt aaaaccttat    600

catattgcag aggaagaaga ggcgaatgcg aagtgcggtc aattcccacg gactttaaac    660

cttaacttcg tgcgtaaaca agctatgcgt tacggcgaaa actcccatca aaatgcggca    720

ttttatgttg atttaaatgt gaaagaagcg agcgtggcta cagctaatca actgcaaggt    780

aaagccttgt cttacaataa tattgccgac actgatgcag cacttgaatg cgtgaaagaa    840

tttgacgatc cagcttgcgt aatcgttaaa catgccaatc catgtggtgt ggcgttaggt    900

aaggatattt tagacgctta taatcgcgct taccaaaccg atccaacgtc tgcttttggc    960

ggcattattg cttttaaccg tgaattagac gaaaaaacgg cgaatgaaat tgtggaacgc   1020

caattcgttg aagtgattat cgcaccgaaa gtttctgctg aagcgcaaga agtaatgaag   1080

cgtaagaaaa atgtgcgttt gcttgaatgt ggtgaatgga cttctcgttc cgaacgtttg   1140

gatttcaaac gtgtaaacgg cggtttatta gtacaagatg cggatttagg tatggttggc   1200

gtggatgatt taaaagtcgt gagtaaacgt cagccaactg aacaagaatt aaaagactt    1260

ttattctgct ggaaagtggc aaaatttgtg aaatcgaatg ccattgttta cgccaaagc    1320

aatcaaacta tcggcattgg tgcaggtcaa atgagccgcg tatattctgc gaagattcg    1380

ggtattaaag cgcaagatga aggtttagaa gtggctggtt gtgtgatggc atctgagcg    1440

ttcttcccat tccgtgacgg cattgatgcg gcggcgaaag tgggtattca atgtggatc    1500

catccaggtg gatcaatgcg cgatcaagaa gtcattgatg cggcggatga acatatatg    1560

gtaatggtat tgactggaat gcgacatttt agacattaa                          1599
```

<210> SEQ ID NO 17
<211> LENGTH: 807
<212> TYPE: DNA
<213> ORGANISM: Haemophilus influenzae

<400> SEQUENCE: 17

```
atgaattcaa attatttact tcttccccac tttgatccga gtatttttac gcttggcgat     60
```

-continued

```
agtaatatcg gcttacgttg gtatggcttg atgtaccttt taggttttgt ttttgcacgt    120

tggcttgcgg ttcgccgtgc taatcgccca aatagcggtt ggacagtaga tcaagttgat    180

agcttacttt tcaacggttt tatgggggtg tttattggcg gacgtgttgg cgatgtattt    240

ttctataatc tcgatcattt cttacaagaa ccactttatt tattccgcgt ttgggaaggt    300

ggaatgtcgt tccacggtgg cttaattggt gtaattgttg ctatgatttg gacatcttat    360

tctcaaaaac gtaatttttg gcaaacggct gattttgttg cgcctttgat tccgtttggt    420

ttaggtttag gcagaattgg taatttcatt aatcttgaac tatggggacg cgaaacgaat    480

gtgccttggg caatgatttt cccgaatgat cctcttttac tgcctcgtca tccatcacaa    540

ctttatgaag cctttttaga aggcctggtg ttgtttacga ttctgaatat ttttattaaa    600

aaaccacgtc caatggcttc tgttgcaggt ttattcttaa ttggttatgg cgtcttccgt    660

tttattgtgg aatatgtgcg tgaacctgaa gttgaaaatt tctttgggat tattacacga    720

gggcaagccc tttgcttgcc gatgattatt ggtggtgctt tcattatggc ttgggcttat    780

tcacgcaaaa gtgcggtcat aaaatag                                         807
```

<210> SEQ ID NO 18
<211> LENGTH: 522
<212> TYPE: DNA
<213> ORGANISM: Haemophilus influenzae

<400> SEQUENCE: 18

```
atggatgcag caaaagtgcg gtcagaattt gacgagaaaa tgatgcgcta cgcccttgag     60

cttgccgata aagcggaagc gttaggtgag attcctgtgg gggcggtgct ggtggatgac    120

gctagaaata ttattggaga aggttggaat ctctccattg ttcaaagtga tcctactgca    180

catgctgaaa ttatcgcttt gcgtaatggt gcgaaaaata ttcaaaatta tcgcctactg    240

aatagcacgc tttatgtgac attagagcct tgcacaatgt gcgcaggggc aattttgcat    300

agccgtatta aacgtcttgt gttcggtgca tctgattata aaactggcgc gattggatca    360

cgttttcatt tttttgatga ttacaagatg aatcatactt tagaggttac atctggcgta    420

ttggcagaag agtgtagtca aaaattgagt acatttttc agaaaagacg cgaggagaaa    480

aaaatagaga aagcattatt aaaaagtctg agtgataagt aa                       522
```

<210> SEQ ID NO 19
<211> LENGTH: 315
<212> TYPE: DNA
<213> ORGANISM: Haemophilus influenzae

<400> SEQUENCE: 19

```
atggaaaaca aggctgagcg ttatcaaaaa gcagtcaata ttacggatgt gcttgagcaa     60

tcgccctttg ccaaaataat caaaaaaggt cttgctatca atgaaatcaa tcaaaaattt    120

aaccgcattt ttccacagga atttcacggc aaatttcgta ttggtaatat gacagataac    180

tcaattttta ttgagacagc aaatgcgatc gttcgccaag gaattttatt cagacagaca    240

gaattgttga aactcattca agaagagttt ccgcaagtaa caggatttga gataacgatc    300

aatcctggat tttaa                                                      315
```

<210> SEQ ID NO 20
<211> LENGTH: 303
<212> TYPE: DNA
<213> ORGANISM: Haemophilus influenzae

<400> SEQUENCE: 20

-continued

```
atgatttcag gcactgtcaa accgaatttt tggtcgcgat tacttttaag tatcatcgca     60

atttttgctt tgcctaacgc acaaagtttt gaaaatcaaa ataatacgga aaattattcc    120

tcaagtgttt ccattcaaca agcgttagaa acggtaaaag ttgctcgtga agtgcaacga    180

caagccattc ctcaaccttc aatttcccgt caaactgaaa aacaacttaa aattcaaccg    240

cacttttta ctgaagcgtt gaatattagc gcgccaattc gagcaggccc cttgcttatt    300

taa                                                                 303
```

<210> SEQ ID NO 21
<211> LENGTH: 2706
<212> TYPE: DNA
<213> ORGANISM: Haemophilus influenzae

<400> SEQUENCE: 21

```
atgagcattt taacaagaat ttttggtagt cgtaatgaac gcgttttacg taaattaaaa     60

aaacaagtcg taaaaattaa taaaatggag cctgcttttg aggcattaag tgatgatgaa    120

ttaaaagcaa aaacacaaga gtttcgtgat cgtttaagtg gtggcgaaac tttgcaacaa    180

attttaccag aagcattcgc aacggtacgc gaagcaagta agcgtgtgct tggtatgcgc    240

cattttgatg ttcagcttat cggtgggatg gtattgacta accgctgtat cgcagaaatg    300

cgtactggtg aaggtaaaac attaacggcg actttgcctt gttatttaat cgcacttgaa    360

ggtaaaggcg ttcacgtggt aaccgtgaat gattatcttg ctcgccgaga tgcagaaaca    420

aaccgtccgt tatttgaatt tttaggcatg agtgtaggcg tcaatattcc tggtttatcg    480

ccagaagaaa aacgtgcagc ttatgcggca gatattactt atgcaaccaa tagtgaactt    540

ggttttgatt atttacgtga caacttagcc cactcaaaag aagagcgttt ccaacgtact    600

ttaggctatg cgttggtgga tgaagtggat tctatcttaa tcgatgaagc gcgtacgcca    660

ttgattattt ctggtcaggc agaaaacagt tcagagcttt atattgcggt aaataaattg    720

atcccaagtt taattaaaca agaaaaagaa gatacggaag aatatcaagg agagggcgat    780

ttcactttag atttgaaatc taaacaagcg catttaaccg aacgtggtca agaaaaagta    840

gaagattggt taattgcaca aggtttaatg cctgaggggg actctttgta ttctcctagt    900

cgaattgtat tgcttcatca cgttatggct gcattgcgtg cgcacacatt gtttgaaaaa    960

gatgtcgatt acattgtgaa ggacggtgaa atcgtgattg ttgatgaaca cactggtcgt   1020

acaatggcgg ggcgtcgttg gtcagatggt ttgcaccaag ccattgaggc aaaagaaggg   1080

gtggatgtta agagcgaaaa ccaaactgtt gcatcaattt cttaccaaaa ctacttccgt   1140

ttatatgaac gtcttgcggg tatgacgggg actgcggata ccgaagcatt tgagttccaa   1200

caaatttatg gcttggaaac tgttgtaatt ccaacaaatc gtccaatgat tcgtgatga    1260

cgcactgatg tgatgtttga aaatgaacaa tataaattta atgcgattat tgaagacat    1320

aaagattgtg tagaacgcca gcaaccagta ttagtgggga cgatttcagt cgaaaaaca    1380

gaagaattat ctaaagcgtt agataaagca ggtataaaac acaatgtgtt gaatgcaaa    1440

ttccaccaac aagaagcgga aatcgtggca gaagcaggat ttcctagcgc agtgatatc    1500

gcaacgaata tggcgggtcg aggtacggat attattcttg gcggtaactg gaaacgcag    1560

gctgccaaat tagaaaatcc aactcaagaa caaattgaag cccttaaagc agatgggag    1620

aaaaaccacg aaattgtaat gaaagcgggt gggttgcata ttatcggtac aggcgtcac    1680

gaatctcgcc gtattgataa ccagttgcgc ggtcgttctg ggcgtcaagg taccccggt    1740
```

-continued tcttctcgtt tctatctttc tttggaagat ggtttaatgc gcatttattt aatgagggt 1800 aagctcaatt taatgcgtaa agcgttcacg gtagcaggcg aggcaatggagtcgaaaatg 1860 ttggcgaaag tgattgcatc tgctcaagca aaagttgagg cgttccatt tgatggccgt 1920 aaaaacctac ttgaatatga tgatgtggca aatgaccaac gtcacgcgt ttatgagcaa 1980 cgcaatcatt tgcttgataa tgatgatatt tctgaaacta tcaacgcat tcgccacgat 2040 gtgtttaatg gtgtgattga tcaatatatt ccaccacaat ctttggaga acaatgggat 2100 attaaagggc ttgaagaacg tttatctcaa gagtttggta tggaatacc gatttctaat 2160 tggttggaag aagataataa tcttcacgaa gaaagtttgc gcgacgcat tgtggaaatt 2220 gcagaaaagg aatacaaaga aaaagaggct ttggttggcg aagcgctat gcgccatttt 2280 gaaaaaggtg ttatgttgca aaccttagat gaactttgga aaaacactt agcttcgatg 2340 gattatttac gccaaggtat tcatttacgt ggctatgccc aaaagatcc aaaacaagag 2400 tataaaaaag aatctttccg tatgtttacg gaaatgttgg ttctttaaa acaccaggtt 2460 atcacggctt taacccgtgt acgtgtgcgt actcaagaagaaatggaaga agctgaacgt 2520 gctcgtcaag aaatggcagc acgtatcaat caaaataat tacctgtgga tgaaaatagt 2580
cagacaactc aaaattcaga gactgaagat tattcagac gtcgcattgg tcgcaacgag 2640
ccttgtcctt gtgggtcggg taaaaaatat aagcatttc acggcagtcg tgtggcacgc 2700
cagtaa 2706

<210> SEQ ID NO 22
<211> LENGTH: 111
<212> TYPE: DNA
<213> ORGANISM: Haemophilus influenzae

<400> SEQUENCE: 22
atgccaaacg aacgtaatat tcaaaattat cactcgactt acaacaacat tcgggattgg 60
cttggttatc aaaaagctgg cgaggaaaaa gcaaagtcga ccatcaatta g 111

<210> SEQ ID NO 23
<211> LENGTH: 279
<212> TYPE: DNA
<213> ORGANISM: Haemophilus influenzae

<400> SEQUENCE: 23
atggatggca tattacgtaa actcatttca attaaggatt tacaccattg cctgcagaaa 60
ttttttgtgg atgaaagaga atctattata gaaatgaatg ataataagct ttcagaacag 120
tttgatttag cattgattga aacgcatggt aaatcaaaaa ttttaaaaaa tttatcttta 180
ttcaaacaaa ccatgtctaa ttatcttact caattatcaa aagataatat gaaagaaaca 240
gaaaatactg ttcataaaat taaaagagta gcagcatag 279

<210> SEQ ID NO 24
<211> LENGTH: 852
<212> TYPE: DNA
<213> ORGANISM: Haemophilus influenzae

<400> SEQUENCE: 24
atgactgatt taaccggaat tttatacatt gttgccacgc ccattggcaa tttacaagat 60
attacccaac gtgctttaga gacttttgct caagtggatt taattgcagc agaagatact 120
cgccatagtg gacttttatt gagccattac ggcattaaga agccattttt tgctttgcac 180
gatcataacg aacaagaaaa agcgcatatt ttggtggaaa agctcaagca ggggagtaat 240

-continued attgccttga tttctgatgc ggggacgcca ttaatcagtg accctggttt tcatttagta 300
cgccaatgcc gtgaagctgg cattcgagtt gtgcctttgc caggagcttg tgcggcaatt 360
accgctcttt gtgcatcggg gattgcttct gatagatttt gttttgaagg ctttttacct 420
gcgaaaagta aagcacgcaa agataaatta gaaaatatcg cagaagaaga ccgcactttg 480
attttttatg aatccactca ccgtatttta gatacactag aagatatgca agcggtgcta 540
ggggaagaac gatacattgt gttagcccgt gaaatgacta aaacttggga aacgattacg 600
gggaatacga ttaaaaattt acgcgaatgg cttttagaag atcccaatcg tacaaaaggc 660
gagatggttt tgattgtgga aggcaaacca aagtctgaca ataacgatga aatttcgccg 720
caagcggtaa aggcacttga gttaattgca gaagaattgc cacttaaaaa agcagcagct 780
atagttgctg agttgtatgg ttataagaag aatgctttgt atcaatttgg attagcgcat 840
ttggaaaaat aa 852

<210> SEQ ID NO 25
<211> LENGTH: 1728
<212> TYPE: DNA
<213> ORGANISM: Haemophilus influenzae

<400> SEQUENCE: 25
atgtctattc tattacaagg cgaacgtttt aaaaaacgtt taatgccaat tttattgtca 60
atggctttag ctggctgttc aaatctactt ggtagcaatt tcacgcaaac cttacaaaaa 120
gatgcaaatg caagttctga attttatata aacaaattag ggcaaacaca agaacttgaa 180
gatcaacaaa cctataaatt gctcgcggct cgagtgttaa tccgtgaaaa taaggttgaa 240
caatcggcag cgttattgag ggaattaggc gaattaaatg atgcgcaaaa attagatcgt 300
gcattaattg aagcgagaat ttctgctgca aaaaatgcca atgaagtcgc acaaaatcaa 360
ttacgtgcat tggatttaaa taaactaagc ccgtcacaaa aatctcgtta ttacgaaacc 420
ttagctattg ttgccgaaaa ccgtaaagac atgattgaag cggtaaaagc gcggatagaa 480
atggataaga atttaacaga tgtacaacgt catcaagata atattgataa aacttgggct 540
ttattgcgtt cagcgaatac tggcgttatt aataatgcct ctgatgaagg taatgcagct 600
ttaggcggtt ggctaacatt aatcaaagcc tacaacgatt atattcgtca gcctgtacaa 660
ttaagccaag ccttacaaag ttggaaaaat gcttatccaa atcatgcagc cgcaacgttg 720
ttcccaaaag aattgcttac attgcttaat ttccaacaaa cgaatgtgtc acaaattggt 780
ttactcttgc cattaagtgg tgacggacaa attcttggca caaccattca atcgggtttt 840
aacgacgcga aaggtaactc aaccattcca gtgcaagtgt ttgatacctc aatgaattct 900
gtccaagata tcattgcgca agcaaaacaa gcggggatta aaccttagt tggcccatta 960 ctaaaacaaa atcttgatgt gattttagca gatcctgctc aaattcaagg tatggatgtg 1020
cttgcattaa atgccacacc aaattctcgt gcgattcctc aactttgtta ttacggactt 1080
tcgccagaag atgaagctga atctgccgcc aataaaatgt ggaacgatgg cgtgcgtaat 1140
ccacttgtcg caatgccgca aaatgattta ggacaacgcg taggcaatgc ctttaatgta 1200
cgttggcaac aattagcagg tactgatgcg aatatccgtt actacaattt gcctgcggat 1260
gtgacctatt tcgttcaaga aaataactca aatacaaccg cactttatgc cgtagcaagt 1320
ccaactgaac tggcagaaat gaaaggttat ttaacaaata tcgtacctaa tttagcgatt 1380
tatgccagtt ctcgagcaag cgcaagtgcg acaaacacta ataccgactt catcgcacag 1440

-continued

```
atgaacggtg tacagtttag tgatattcca ttttttaaag ataccaattc tccacaatat   1500

cagaagttag caaaatccac gggggcgaa tatcaattga tgcgtttata tgcaatgggt   1560

gcggatgcgt ggttgctcat taatcaattt aatgaattac gccaagtgcc aggctatcgc   1620

ttgagtggct taacagggat tttaagtgct gataccaact gtaatgttga acgcgatatg   1680

acttggtatc aatatcaaga tggtgcaatt gtaccagttg caaactaa               1728
```

<210> SEQ ID NO 26
<211> LENGTH: 347
<212> TYPE: DNA
<213> ORGANISM: Streptococcus pneumoniae

<400> SEQUENCE: 26

```
tcatggcaaa tcatttccgt acagatcgtg tgggcatgga aatcaagcgt gaagtcaatg     60

agattttgca aaagaaagtc cgtgatccac gtgtccaagg tgtgaccatc atagatgttc    120

agatgctggg tgacttgtct gttgccaagg tttattacac cattttgagt aaccttgctt    180

cggataacca aaaagcccaa atcgggcttg aaaaagcaac tggtaccatc aaacgtgaac    240

ttggtcgcaa tttgaaattg tacaaaatcc cagatttgac cttcgtcaaa gacgagtcca    300

tcgagtatgg aaacaagatt gacgagatgc tacgcaatct ggataag                  347
```

<210> SEQ ID NO 27
<211> LENGTH: 2787
<212> TYPE: DNA
<213> ORGANISM: Streptococcus pneumoniae

<400> SEQUENCE: 27

```
ggatgtgaaa agccactcat caagtgtgga agaagctgtc gctgcaaaaa ttgctgccag     60

ctttaagcct gcagctgctc cgaaagtaga agcaaaacct gcagccccaa aagtaagtgc    120

agaaaagaaa gccgaaaaat ctgagccagc taaaccagct gtagctaagg aagaggcaaa    180

acctgcagcc ccaaaagcaa gtgcagaaaa gaaagccgaa aagtctgaac cagtaaaacc    240

agctgtagcc aaggaagagg caaaaccagc tgagccagtc actccgaaaa cagaaaaagt    300

agcggctaaa ccgcaaagtc gtaatttcaa ggctgagcgt gaagcacgtg ctaaagagca    360

ggcagagcga cgcaagcaaa ataagggcaa taaccgtgac caacaacaaa acggaaaccg    420

tcagaaaaac gacggccgta atggtggaaa acaaggtcaa agcaaccgcg acaatcgtcg    480

ctttaatgac caagctaaga agcagcaagg tcagcaaaaa cgtagaaatg agcgccgtca    540

gcaagaggat aaacgttcaa atcaagcggc tccacgtatt gactttaaag cccgtgcagc    600

agccctaaaa gcagagcaaa atgcagagta cgctcgttca agtgaggaac gcttcaagca    660

gtatcaggct gctaaagaag ccttggctca agctaacaaa cgcaaggaac cagaggaaat    720

ctttgaagaa gcggctaagt tagctgaaca agcacagcaa gttcaagcag tggttgaagt    780

cgtccctgag aaaaaagaac ctgcagtgga tacacgtcgt aaaaaacaag ctcgaccaga    840

caaaaatcgt gacgattatg atcatgaaga agatggtcct agaaaacaac aaaagaatcg    900

aagtagtcaa aatcaagtga gaaatcaaaa gaatagtaac tggaataaca acaaaaagaa    960

caaaaaaggc aataacaaga acaaccgtaa tcagactcca aaacctgtta cggagcgtaa   1020

attccatgaa ttgccaacag aatttgaata tacagatggt atgaccgttg cggaaatcgc   1080

aaaacgtatc aaacgtgaac cagctgaaat tgttaagaaa cttttcatga tgggtgtcat   1140

ggccacacaa aaccaatcct tggatgggga aacaattgaa ctcctcatgg tggattacgg   1200

tatcgaagcc aaacaaaagg ttgaagtgga taatgctgac atcgaacgtt tctttgtcga   1260
```

-continued agatggttat ctcaatgaag atgaattggt tgagcgtcca ccagttgtta ctatcatggg 1320
acacgttgac cacggtaaaa caaccctttt ggatactctt cgtaactcac gtgttgcgac 1380
aggtgaagca ggtggtatta ctcagcatat cggtgcctac caaatcgtgg aaaatggtaa 1440
gaagattacc ttccttgata caccaggaca cgcggccttt acatcaatgc gtgcgcgtgg 1500
tgcttctgtt accgatatta cgatcttggt cgtagcggca gatgacgggg ttatgcctca 1560
gactattgaa gccatcaacc actcaaaagc agctaacgtt ccaatcatcg tagctattaa 1620
caagattgat aaaccaggtg ctaacccaga acgcgttatc ggtgaattgg cagagcatgg 1680
tgtgatgtca actgcttggg gtggagattc tgaatttgtt gaaatttcgg ctaaattcaa 1740
ccaaaatatc gaagaattgt tggaaacagt ccttcttgtg gctgaaatcc aagaactcaa 1800
agcagaccca acagttcgtg cgatcggtac ggttatcgaa gcgcgcttgg ataaaggaaa 1860
aggtgcggtc gcaacccttc ttgtacaaca aggtaccttg aatgttcaag acccaatcgt 1920
tgtcggaaat acttcggtcg tgtccgtgct atgaccaacg accttggtcg tcgtgttaaa 1980
gttgctggac catcaacacc agtctctatc acaggtttga acgaagcacc gatggcgggt 2040
gaccactttg ccgtttacga ggatgaaaaa tctgcgcgtg cagcaggtga agagcgtgcc 2100
aaacgtgccc tcatgaaaca acgtcaagct acccaacgtg ttagccttga aaacctcttt 2160
gataccctta aagctgggga actcaaatct gttaatgtta tcatcaaggc tgatgtacaa 2220
ggttctgttg aagccctttc tgcctcactt caaaagattg acgtggaagg tgtcaaagtg 2280
actatcgtcc actcagcggt cggtgctatc aacgaatcag acgtgaccct tgccgaagct 2340
tcaaatgcct ttatcgttgg tttcaacgta cgccctacac cacaagctcg tcaacaagca 2400
gaagctgacg atgtggaaat ccgtcttcac agcattatct acaaggttat cgaagagatg 2460
gaagaagcta tgaaagggat gcttgatcca gaatttgaag aaaaagttat tggtgaagcg 2520
gttatccgtg aaaccttcaa ggtgtctaaa gtgggaacta tcggtggatt tatggttatc 2580
aacggtaagg ttgcccgtga ctctaaagtc cgtgttatcc gtgatggtgt cgttatctat 2640
gatggtgaac tcgcaagctt gaaacactat aaagacgacg tgaaagaagt gacaaacggt 2700
cgtgaaggtg gattgatgat cgacggctac aatgatatta agatggatga tgtgattgag 2760
gcgtatgtca tggaagaaat caagaga 2787

<210> SEQ ID NO 28
<211> LENGTH: 294
<212> TYPE: DNA
<213> ORGANISM: Streptococcus pneumoniae

<400> SEQUENCE: 28
aataagcaaa agataagtaa tctcttgggg cttgctcagc gagcagggcg catcatatcg 60
ggtgaagaat tggtggtcaa ggccattcaa gacggcaagg ccaagttggt ctttctagct 120
catgatgctg gacccaatct gaccaagaag attcaagata aaagtcatta ttatcaagta 180
gaaattgtaa ccgtgttttc aacactggaa ttaagcatag cagtcgggaa atcgagaaag 240
gttttggctg taacagatgc tggatttaca aagaaaatga ggtctcttat ggaa 294

<210> SEQ ID NO 29
<211> LENGTH: 1070
<212> TYPE: DNA
<213> ORGANISM: Streptococcus pneumoniae

<400> SEQUENCE: 29

-continued

```
atgagtaaag aaatgctaga ggccttccgc attttggaag aagacaaggg aatcaaaaaa     60
gaagatatca tcgacgcagt agtagagtcg cttcgttccg cttatcgcag acgctatggt    120
cagtcagaca gcgtagctat tgacttcaac gaaaaaacag gtgactttac agtttatact    180
gtccgtgaag ttgttgatga agtatttgat agccgtttgg aaatcagctt gaaagatgct    240
cttgccatta attcagctta tgaacttgga gacaaaatca agtttgaaga agcaccagct    300
gagtttggtc gtgtagcagc ccaatctgcc aaacaaacca tcatggaaaa aatgcgcaac    360
aaacacgtgc catcacttac aatacttaca aagaacatga gcaagaaatc atgtctggta    420
cagtagaacg ctttgacaac cgctttatct atgtcaacct tggtagcatc gaagcccaat    480
tgtcaaaaca agaccaaatt cctggagaag tttttgcttc tcatgatcgt atcgaagttt    540
atgtttacaa ggttgaagac aaccctcgtg gtgtgaacgt ctttgttagc cgtagtcatc    600
cagaaatgat caaacgttta atggagcaag aaattccaga agtttatgat ggaactgttg    660
aaatcatgag cgtggctcgt gaagcaggtg accgtacgaa ggttgctgtt cgtagccaca    720
atccaaacgt ggatgctatc ggtacaatcg ttggacgtgg tggtgctaat atcaagaaga    780
ttactagcaa attccaccca gctcgttacg atgctaaaaa tgaccgcatg gtaccaatcg    840
aagaaaatat cgatgttatc gagtgggtag cagatccagc tgaatttatc tacaatgcca    900
tcgctcctgc tgaggttgac caagttatct ttgatgaaaa cgacagcaaa cgtgccttgg    960
tggttgttcc agataacaag ctttctcttg ccattggtcg tcgtggacaa aacgtgcgct   1020
tggcggctca cttgactggt taccgtatcg atatcaagtc tgctagcgaa              1070
```

SYSTEMATIC IDENTIFICATION OF ESSENTIAL GENES BY IN VITRO TRANSPOSON MUTAGENESIS

CROSS-REFERENCE TO RELATED APPLICATIONS

This application claims benefit from provisional application "Systematic identification of essential genes by in vitro transposon mutagenesis" (U.S. Ser. No. 60/079,770), filed March 27, 1998.

STATEMENT AS TO FEDERALLY SPONSORED RESEARCH

This research has been sponsored in part by NIH grants AI02137 and AI26289. The government has certain rights to the invention.

BACKGROUND OF THE INVENTION

Nearly 40% of the *Haemophilus* (*H.*) *influenzae* genome is comprised of genes of unknown function, many of which have no recognizable functional orthologues in other species. Similar numbers of unidentified open reading frames (orfs) are present in other sequenced or partially sequenced genomes of infectious organisms. Comprehensive screens and selections for identifying functional classes of genes provide a crucial starting point for converting the vast body of growing sequence data into meaningful biological information that can be used for drug discovery.

One major and important class of genes consists of those bacterial genes that are essential for growth or viability of a bacterium. Because useful conventional antibiotics are known to act by interfering with the products of essential genes, it is likely that the discovery of new essential gene products will have a significant impact on efforts to develop novel antimicrobial drugs. Essential gene products have been traditionally identified through the isolation of conditional lethal mutants, or by transposon mutagenesis in the presence of a complementing wild type allele (balanced lethality). However, such approaches are laborious, as they require identification, purification, and study of individual mutant strains. These methods are also limited to species with well-developed systems for genetic manipulation and, therefore, cannot be readily applied to many of the potentially dangerous microorganisms whose genomes have recently been sequenced.

In order to facilitate the discovery of novel anti-microbial drugs, it would be desirable to have a rapid, generalized method of identifying essential growth/viability genes in pathogens. Such a method would be particularly useful for identifying essential genes in pathogens that are not genetically well-characterized. Such a method could also be used to identify essential genes in higher organisms, e.g., in animals and in plants.

SUMMARY OF THE INVENTION

We have developed a general system for the identification of essential genes in organisms. The system may be used to discover novel target genes for the development of therapeutic compounds, as well as for the discovery of genes that are involved in cell growth or viability. A related aspect of the invention allows for rapid construction of conditional mutations in essential genes.

In general, the invention features a method for locating an essential region in a portion of DNA from the genome of an organism. The method includes: a) mutagenizing DNA having the sequence of an essential portion of DNA, wherein the mutagenizing is performed using in vitro mutagenesis with a transposon; b) transforming cells of the organism with the mutagenized DNA of step a); c) identifying cells containing the mutagenized DNA; and d) locating the essential region of the DNA portion by detecting the absence of transposons in the essential region of DNA in cells containing the mutagenized DNA.

In various embodiments, the transposon may contain a selectable marker, the transposon may be mariner, and the method may further comprise the use of Himar 1 transposase.

In a preferred embodiment, the in vitro mutagenesis is high saturation mutagenesis. In further embodiments, the portion of DNA may be amplified using the polymerase chain reaction (PCR) prior to mutagenesis, or the portion of DNA may be cloned into a vector prior to mutagenesis. In another embodiment, prior to transforming the cells, the mutagenized DNA may be subjected to gap repair using DNA polymerase and DNA ligase. In still another embodiment, the transposon-mutagenized DNA may be recombined into the chromosome using an allelic replacement vector.

In another preferred embodiment, the locating of an essential region of DNA is done by performing PCR footprinting on a pool of transposon-mutagenized cells. The PCR footprinting is performed using a primer that hybridizes to the transposon, plus a primer that hybridizes to a specific location on the chromosome, after which the PCR products are separated on a footprinting gel. A PCR product on the gel represents a region of the chromosome that does not contain an essential gene, and the lack of a PCR product in an area of the gel, where a PCR product is expected, represents a region of the chromosome that contains an essential gene. Alternatively, a low level of the PCR product on the gel, relative to other PCR products on the gel, represents a region of the chromosome that contains an essential gene.

In still other embodiments, the cell may have a haploid growth phase, or be a single-cell microorganism, or be naturally competent for transformation, or be made competent for transformation, or be a fungus, such as a yeast (e.g., *Saccharomyces cerevisiae*), or be a bacterium, including, but not limited to, a gram-positive bacterium. In a preferred embodiment, the bacterium is to be selected from the group consisting of:*Actinobacillus actinomycetemcomitans; Borrelia burgdorferi; Chlamydia trachomatis; Enterococcus faecalis; Escherichia coli; Haemophilus influenzae; Helicobacter pylori; Legionella pneumophila; Mycobacterium avium; Mycobacterium tuberculosis; Mycoplasma genitalium; Mycoplasma pneumonia; Neisseria gonorrhoeae; Neisseria meningitidis; Staphylococcus aureus; Streptococcus pneumoniae; Streptococcus pyogenes; Treponema pallidum*; and *Vibrio cholerae.*

In another embodiment, the transposon may contain a selectable marker gene, and identifying the cells containing mutagenized DNA may be based upon the ability of the cells to grow on selective medium, wherein a cell containing a transposon can grow on selective medium, and a cell lacking a transposon cannot grow, or grows more slowly, on selective medium.

In still another embodiment, the transposon may contain a reporter gene, and identifying cells containing mutagenized DNA may be based on a reporter gene assay, wherein a cell confirming a transposon expresses the reporter gene and a cell lacking a transposon does not express the reporter gene.

In yet another embodiment, the method includes a step in which the cells are cultured in a medium that approximates a host environment for a pathogen.

In a second aspect, the invention provides a method for obtaining conditional mutations in essential genes. The method includes the steps of amplifying DNA containing a selective marker, as described herein, near an essential gene (e.g., a transposon) using mutagenic amplification (e.g., mutagenic PCR), transforming the DNA into a competent host under conditions allowing selection for those strains containing the selective marker, and screening for strains under permissive and non-permissive conditions such that conditional lethal mutations may be identified.

In a third aspect, the invention provides a method for isolating a compound that modulates the expression of a nucleic acid sequence operably linked to a gene promoter. The method includes a) providing a cell expressing a nucleic acid sequence operably linked to a gene promoter, wherein the gene promoter is the gene promoter for: HI0455; HI0456; HI0458; HI0599; HI0887; HI0904; HI0906; HI0907; HI0908; HI0909; HI1650; HI1651; HI1654; HI1655*; S. pneumoniae* rbfA; *S. pneumoniae* IF-2*; S. pneumoniae* L7AE; or *S. pneumoniae* nusA; b) contacting the cell with a candidate compound; and c) detecting or measuring expression of the gene following contact of the cell with the candidate compound.

In preferred embodiments of the third aspect, the nucleic acid sequence is a reporter gene (e.g., GFP, lacZ, or alkaline phosphatase) or is HI0455; HI0456; HI0458; HI0599; HI0887; HI0904; HI0906; HI0907; HI0908; HI0909; HI1650; HI1651; HI1654; HI1655*; S. pneumoniae* rbfA; *S. pneumoniae* IF-2*; S. pneumoniae* L7AE; or *S. pneumoniae* nusA.

In yet another preferred embodiment of the third aspect, the modulation in the expression of the nucleic acid sequence modulates cell growth or viability of the cell.

In a fourth aspect, the invention provides a method for identifying a nucleic acid sequence that is essential for cell growth or viability. The method includes a) expressing in a cell (i) a first nucleic acid sequence operably linked to a gene promoter, wherein the gene promoter is the gene promoter for: HI0455; HI0456; HI0458; HI0599; HI0887; HI0904; HI0906; HI0907; HI0908; HI0909; HI1650; HI1651; HI1654; HI1655*; S. pneumoniae* rbfA; *S. pneumoniae* IF-2*; S. pneumoniae* L7AE; or *S. pneumoniae* nusA; and (ii) a second nucleic acid sequence; and b) monitoring the expression of the first nucleic acid sequence, wherein an increase in the expression identifies the second nucleic acid sequence as being essential for cell growth or viability.

In preferred embodiments of the fourth aspect, the first nucleic acid sequence is a reporter gene (eg., GFP, lacZ, or alkaline phosphatase), or is HI0455; HI0456; HI0458; HI0599; HI0887; HI0904; HI0906; HI0907; HI0908; HI0909; HI1650; HI1651; HI1654; HI1655*; S. pneumoniae* rbfA; *S. pneumoniae* IF-2*; S. pneumoniae* L7AE; or *S. pneumoniae* nusA.

In another embodiment of the fourth aspect, the increase in the expression of the nucleic acid sequence increases cell growth or viability of the cell.

In preferred embodiments of the third or fourth aspect, the expression nucleic acid sequence is measured by assaying the protein level or the RNA level of the nucleic acid sequence.

In other preferred embodiments of the third or fourth aspect, the cell is a single-cell microorganism or the microorganism is a bacterium (e.g., a gram-positive bacterium). A preferred bacterium is one that is selected from the group consisting of: *Actinobacillus actinomycetemcomitans; Borrelia burgdorferi; Chlamydia trachomatis; Enterococcus faecalis; Escherichia coli; Haemophilus influenzae; Helicobacter pylori; Legionella pneumophila; Mycobacterium avium; Mycobacterium tuberculosis; Mycoplasma genitalium; Mycoplasma pneumonia; Neisseria gonorrhoeae; Neisseria meningitidis; Staphylococcus aureus; Streptococcus pneumoniae; Streptococcus pyogenes; Treponema pallidum*; and *Vibrio cholerae.*

By "cells of an organism" is meant cells that undergo homologous recombination. Such cells may be of bacterial, mycobacterial, yeast, fungal, algal, plant, or animal origin.

By "homologous recombination" is meant a process by which an exogenously introduced DNA molecule integrates into a target DNA molecule in a region where there is identical or near-identical nucleotide sequence between the two molecules. Homologous recombination is mediated by complementary base-pairing, and may result in either insertion of the exogenous DNA into the target DNA (a single cross-over event), or replacement of the target DNA by the exogenous DNA (a double cross-over event). Such events may occur in virtually any normal cell, including bacterial, mycobacterial, yeast, fungal, algal, plant, or animal cells.

By "transposon" is meant a DNA molecule that is capable of integrating into a target DNA molecule, without sharing homology with the target DNA molecule. The target molecule may be, for example, chromosomal DNA, cloned DNA, or PCR-amplified DNA. Transposon integration is catalyzed by transposase enzyme, which may be encoded by the transposon itself, or may be exogenously supplied. One example of a transposon is mariner. Other examples include Tn5, Tn7 and Tn10.

By "in vitro transposition" is meant integration of a transposon into target DNA that is not within a living cell. In an in vitro transposition reaction, the transposon integrates into the target DNA randomly, or with near randomness; that is, all DNA regions in the target DNA have approximately equal chances of being sites for transposon integration.

By "selectable marker" is meant a gene carried by a transposon that alters the ability of a cell harboring the transposon to grow or survive in a given growth environment relative to a similar cell lacking the selectable marker. Such a marker may be a positive or negative selectable marker. For example, a positive selectable marker (e.g., an antibiotic resistance or auxotrophic growth gene) encodes a product that confers growth or survival abilities in selective medium (e.g., containing an antibiotic or lacking an essential nutrient). A negative selectable marker, in contrast, prevents transposon-harboring cells from growing in negative selection medium, when compared to cells not harboring the transposon. A selectable marker may confer both positive and negative selectability, depending upon the medium used to grow the cell. The use of selectable markers in prokaryotic and eukaryotic cells is well known by those of skill in the art.

By "permissive growth conditions" or "rich growth conditions" is meant an environment that is relatively favorable for cell growth and/or viability. Such conditions take into account the relative availability of nutrients, the absence of toxins, and optimal temperature, atmospheric pressure, presence or absence of gases (such as oxygen and carbon dioxide), and exposure to light, as required by the organism being studied. Permissive growth conditions may exist in vitro (such as in liquid and on solid culture media) or in vivo (such as in the natural host or environment of the cell being studied).

By "stringent growth conditions" is meant an environment that is relatively unfavorable for growth and/or viability of cells of an organism. An unfavorable environment may be due to nutrient limitations (e.g., as seen with "minimal" bacterial growth medium such as MIc), the presence of a compound that is toxic for the cell under study, an environmental temperature, gas concentration, light intensity, or atmospheric pressure that is extreme (e.g., either too high or too low) for optimal growth/viability of the organism under study.

By "gene that is essential for growth and/or viability" or by "essential gene" or by "essential region in a portion of DNA" is meant a DNA element such as an origin of replication or a gene that encodes a polypeptide or RNA whose function is required for survival, growth, or mitosis/meiosis of a cell. Insertion of a transposon into an essential gene may be lethal, i.e., prevent a cell from surviving, or it may prevent a cell from growing or undergoing mitosis/meiosis. Alternatively, insertion of a transposon into an essential gene may allow survival of a cell, but result in severely diminished growth or metabolic rate. An essential gene also may be conditionally essential (i.e., required for viability and/or growth under certain conditions, but not under other conditions).

By "absence of transposons" is meant that fewer transposon insertions are detected in an essential region of DNA, relative to the number of transposon insertions detected in a non-essential region of DNA. An absence of transposons may be absolute (i.e., zero transposons detected) or relative (i.e., fewer transposons detected).

By "transformation" is meant any method for introducing foreign molecules, such as DNA, into a cell. Lipofection, DEAE-dextran-mediated transfection, microinjection, protoplast fusion, calcium phosphate precipitation, retroviral delivery, electroporation, natural transformation, and biolistic transformation are just a few of the methods known to those skilled in the art which may be used. For example, biolistic transformation is a method for introducing foreign molecules into a cell using velocity driven microprojectiles such as tungsten or gold particles. Such velocity-driven methods originate from pressure bursts which include, but are not limited to, helium-driven, air-driven, and gunpowder-driven techniques. Biolistic transformation may be applied to the transformation or transfection of a wide variety of cell types and intact tissues including, without limitation, intracellular organelles (e.g., and mitochondria and chloroplasts), bacteria, yeast, fungi, algae, plant tissue, cultured cells, and animal tissue and cultured cells.

By "identifying cells containing mutagenized DNA" is meant exposing the population of cells transformed with transposon-mutagenized DNA to selective pressure (such as growth in the presence of an antibiotic or the absence of a nutrient) consistent with a selectable marker carried by the transposon (e.g., an antibiotic resistance gene or auxotrophic growth gene known to those skilled in the art). Identifying cells containing mutagenized DNA may also be done by subjecting transformed cells to a reporter gene assay for a reporter gene product encoded by the transposon. Selections and screens may be employed to identify cells containing mutagenized DNA, although selections are preferred.

By "reporter gene" is meant any gene which encodes a product whose expression is detectable and/or quantitatable by immunological, chemical, biochemical, biological, or mechanical assays. A reporter gene product may, for example, have one of the following attributes, without restriction: fluorescence (e.g., green fluorescent protein), enzymatic activity (e.g., lacZ/β-galactosidase, luciferase, chloramphenicol acetyltransferase, alkaline phosphatase), toxicity (e.g., ricin), or an ability to be specifically bound by a second molecule (e.g., biotin or a detectably labelled antibody). It is understood that any engineered variants of reporter genes, which are readily available to one skilled in the art, are also included, without restriction, in the foregoing definition.

By "allelic replacement vector" is meant any DNA element that can be used to introduce mutations into the genome of a target cell by specific replacement of a native gene with a mutated copy. For example, gene replacement in bacteria is commonly performed using plasmids that contain a target gene containing a mutation and a negative selectable marker outside of the region of homology. Such a plasmid integrates into the target chromosome by homologous recombination (single cross-over). Appropriate selection yields cells that have lost the negative selection marker by a second homologous recombination event (double cross-over) and contain only a mutant copy of the target gene.

By "high saturation mutagenesis" is meant a transposon insertion frequency of at least three insertions per kilobase of target DNA, preferably, at least four insertions per kilobase of target DNA, more preferably at least five or six insertions per kilobase, and most preferably, at least seven or eight transposon insertions per kilobase of target DNA.

By "locating an essential region in a portion of DNA" is meant determining that a given stretch of DNA contains a gene that is necessary for cell growth and/or viability. Such a gene may be necessary under all, or only under some (e.g., stringent) growth conditions. The locating may be done, for example, by PCR footprinting.

The invention provides a method for the rapid identification of essential or conditionally essential DNA segments. The method is applicable to any species of cell (e.g., microbial, fungal, algal, plant, animal) that is capable of being transformed by artificial means, for example, by electroporation, liposomes, calcium phosphate, DEAE dextran, calcium chloride, etc., and is capable of undergoing homologous DNA recombination. This system offers an enhanced means of ascribing important functions to the growing number of uncharacterized genes catalogued in sequence databases.

Other features and advantages of the invention will be apparent from the following description of the preferred embodiments thereof, and from the claims.

BRIEF DESCRIPTION OF THE DRAWINGS

In FIG. 3A, the positions of molecular weight standards are indicated; other panels are labeled with locus names by HI number. In FIGS. 3C and 3D, cells were selected on BXV, MIc, or BXV containing trimethoprim ("Tri"). In FIG. 3F, in vitro mutagenesis of a chromosomal fragment that included the secA gene was performed, and the mutagenized DNA was transformed into both wild-type *H. influenzae* and an *H. influenzae* strain containing pSecA.

FIGS. 5A–5R show the nucleotide and polypeptide sequence of genes found using in vitro transposition mutagenesis to be essential genes.

DETAILED DESCRIPTION OF THE INVENTION

Here we describe a simple system for performing transposon mutagenesis to rapidly identify essential or conditionally essential DNA segments. The technique, termed GAMBIT (Genomic Analysis and Mapping By in vitro Transposition), combines extended-length PCR, in vitro transposition, and PCR footprinting, to screen for genes required for growth. This system takes advantage of the ability of naturally competent cells such as bacteria to efficiently take up DNA added to cultures and incorporate it by homologous recombination into their chromosome. Since mutagenesis is conducted in vitro, there are no host-specific steps in the procedure, making it generally applicable to any naturally transformable species.

Figure 1A:
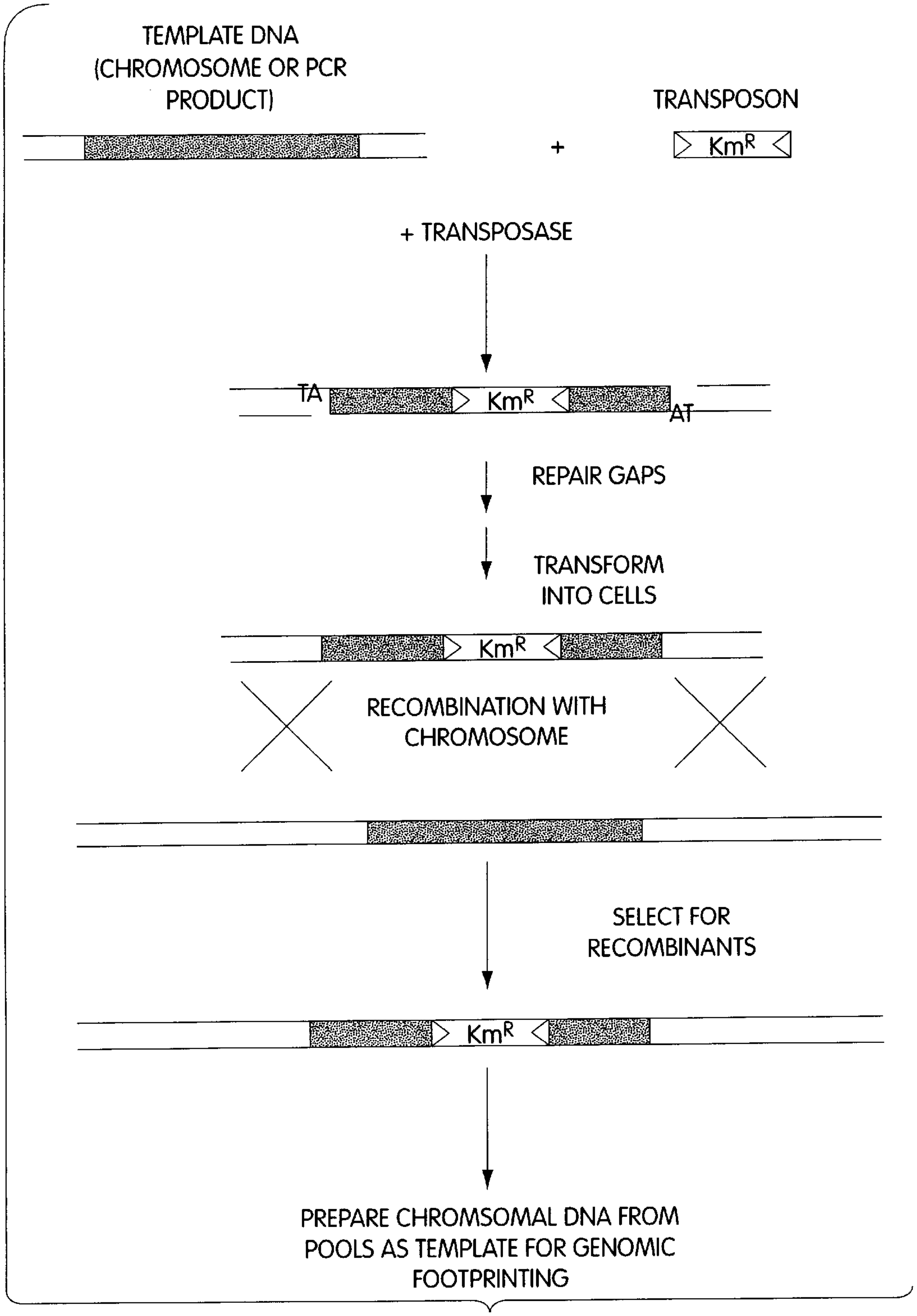
FIG. 1A shows the strategy for producing chromosomal mutations using in vitro transposition mutagenesis.

The first step in the development of the GAMBIT method was to develop an in vitro mutagenesis protocol that could be used on isolated chromosomal DNA derived from a naturally competent bacterial species (FIG. 1A). To test our system we chose *H. influenzae* and *Streptococcus* (*S.*) *pneumoniae*, both of which are transformable, as test organisms, and the mariner transposon Himar1, originally isolated from the horn fly, *Haemotobia irritans* (D. J. Lampe et al., *EMBO J.* 15:5470–5479 (1996); herein incorporated by reference). As will be described in detail below, GAMBIT analysis of ~50 kilobases of *H. influenzae* and 10 kilobases of *S. pneumoniae* DNA confirmed the essential nature of nine of nine known essential genes.

The mariner transposon offers two advantages. First, mariner transposition occurs efficiently in vitro and does not require cellular cofactors. Second, under the conditions we used, mariner shows very little insertion site specificity, requiring only the dinucleotide TA in the target sequence (and even this minor site specificity can be easily altered using different in vitro reaction conditions).

Chromosomal DNA was isolated and mutagenized with the Himar1 transposase and an artificial minitransposon encoding the gene for either kanamycin (magellan1) or chloramphenicol (magellan2) resistance. Insertion of the transposon produces a short single-stranded gap on either end of the insertion site. Since *H. influenzae* and *S. pneumoniae* are known to take up single stranded DNA, these gaps required repair (using a DNA polymerase and a DNA ligase) to produce the flanking DNA sequence required for recombination into the chromosome. The mutagenized DNA was transformed into bacteria, and cells which had acquired transposon insertions by homologous recombination were selected on the appropriate antibiotic-containing medium.

Figure 1B:
FIG. 1B shows a Southern blot analysis of *H. influenzae* transposon mutants. Genomic DNA was isolated from 16 individual mutants and was digested with AseI, which cleaves once within magellan1. Digested DNA was subjected to agarose gel electrophoresis, transferred to nitrocellulose, and then hybridized with a probe composed solely of magellan1 minitransposon-derived DNA.

Using this method, we were able to produce libraries with ~9,000 *H. influenzae* mutants and ~100,000 *S. pneumoniae* mutants, indicating, as predicted, that this approach is equally effective in gram-positive and gram-negative bacteria. Southern blot analysis of AseI-digested DNA from 16 individual *H. influenzae* transposon mutants (FIG. 1B) revealed that each had only a single transposon insertion and that the transposon could insert at a variety of sites. Mutagenesis of *H. influenzae* using in vitro transposition has been recently described using Tn7, although it has not previously been applied to gram-positive organisms.

Although mutant libraries such as those created by the above steps are quite useful for obtaining a given mutant, the GAMBIT technique works best with a greater degree of saturation of mutations to yield a high-density insertion map of a given chromosomal region. To conduct such highly-saturated mutagenesis we targeted specific genomic segments for transposition. First, oligonucleotide primers were synthesized and used to amplify ~10 kb regions of the chromosome, using the polymerase chain reaction (PCR). The resulting PCR products were purified and used as templates for in vitro mariner transposon mutagenesis. Each mutagenized pool of DNA was transformed into competent bacteria and plated on rich medium containing appropriate antibiotic, resulting in libraries of ~400–800 mutants, all of which contained insertions within the target chromosomal segment.

Figure 2:
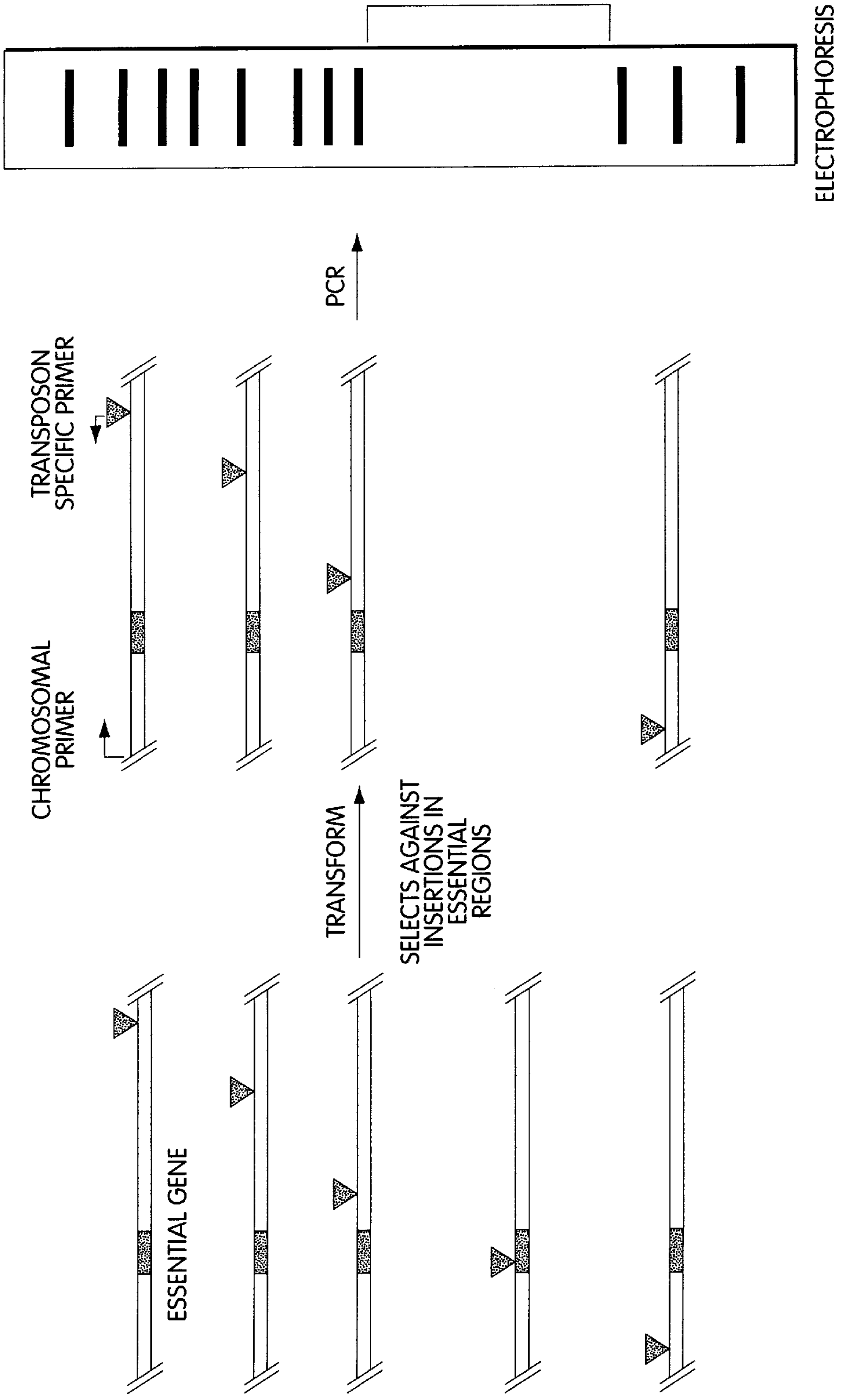
FIG. 2 shows a schematic diagram of PCR footprinting for detection of essential genes. Target DNA mutagenized in vitro with the Himar1 transposon was introduced into bacteria by transformation and homologous recombination. Recombinants were selected for drug resistance encoded by the transposon, and insertions in essential genes were lost from the pool during growth. PCR with primers that hybridized to the transposon and to specific chromosomal sites yielded a product corresponding to each mutation in the pool. DNA regions containing no insertions yielded a blank region on electrophoresis gels.

The position of each of these insertion mutations with respect to any given PCR primer, designed from genome sequence data, can then be assessed by PCR footprinting (or similar procedures) conducted on the entire pool of mutants, using a primer which hybridizes to the transposon and another primer which hybridizes to a specified location in the chromosome (FIG. 2). After amplification, products are analyzed by agarose gel electrophoresis. Each band on the agarose gel represents a transposon insertion a given distance from the chromosomal primer site. Insertions into regions which produce significant growth defects are then represented by areas of decreased intensity on the footprinting gel. Note that either one of the two primers used for amplifying a genomic segment can also be used to analyze mutations within that segment by genomic footprinting.

As an alternative to using PCR products as substrates for in vitro transposition of naturally competent organisms, a high-density insertion map of a given chromosomal region also may be obtained by performing in vitro transposition upon genomic DNA cloned into a vector, for example a cosmid, phage, plasmid, YAC (yeast artificial chromosome), or BAC (bacterial artificial chromosome) vector. Similar high-density mutagenesis can be performed in non-naturally competent organisms using genomic DNA cloned into an allelic replacement vector.

Figure 3A:
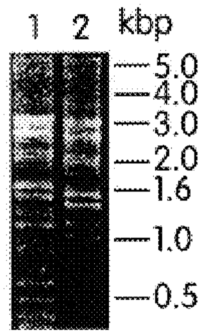
FIGS. 3A–3G show genetic footprinting of *H. influenzae* mutant pools. Genetic footprinting was carried out by using a Himar1-specific primer and a chromosomal primer.

Lane 1 of FIG. 3A shows the analysis by agarose gel electrophoresis of the PCR products obtained from a region of the *H. influenzae* chromosome chosen for GAMBIT analysis. Areas of the gel corresponding to DNA regions that carry many mariner insertions contain many bands; blank regions on the gel, in contrast, correspond to segments of the chromosome that are devoid of mariner insertions. That the banding pattern seen in lane 1 reflects an accurate assessment of the position of insertion mutations within the targeted segment can be shown by simply moving the chromosomal primer by 114 bp (lane 2). Bands and blank regions on the gel are shifted down in migration by a distance corresponding to approximately 114 bases (molecular weights in kilobase pairs (kbp) are indicated at the right). In addition, sequencing of several gel-purified bands demonstrated that they were in the predicted loci.

Figure 3B:
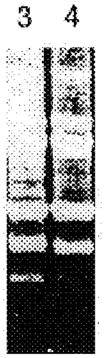

GAMBIT footprinting results are quite reproducible; when two independent insertion libraries are created for a given region, the pattern exhibits only minor differences and the blank regions are unchanged (FIG. 3B, lane 3 vs. lane 4).

Figure 3C:
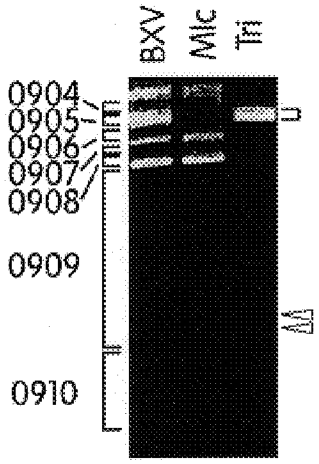
Figure 3D:
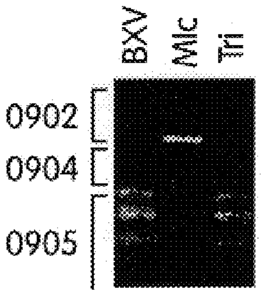

FIG. 3C demonstrates the use of GAMBIT to examine essential genes in the chromosome region containing a *H. influenzae* homologue of the *E. coli* gene thyA, which encodes thymidylate synthetase. Mutation of the thyA gene prevents growth on minimal medium lacking thymidine, but confers resistance to trimethoprim. Thus, this gene provided us with the opportunity to directly test the fidelity of the system, since mutations in thyA can be both positively and negatively selected. A primer which hybridizes 3' to the *H. influenzae* secA gene, 5,159 bp from the thyA gene, was used as a chromosomal primer. When libraries selected on rich medium (BXV) are analyzed by genomic footprinting, the region corresponding to the thyA gene (FIG. 3C, indicated by brackets on the right) contains multiple bands. When the analysis is performed on the same mutant pool plated on a defined medium lacking thymidine (MIc), the thyA region PCR products are no longer seen. Since thyA mutants are resistant to the antibiotic trimethoprim, selection of the same pool on a medium containing trimethoprim ("Tri", 5 $\mu$g/ml) and thymidine followed by PCR analysis yields products only in the thyA region, confirming the identity of the bands seen in this region of the gel. Analysis of the same mutant pool with a primer which hybridizes close to the thyA gene demonstrates that the wide band seen in lane "Tri" can be resolved into a series of bands that correspond to multiple mariner inserts in the thyA gene (FIG. 3D).

Figure 3E:
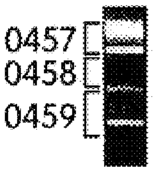

We have found several DNA regions with a decreased number and intensity of PCR products. Some regions contained no detectable PCR products. For example, no bands could be seen in the region in *H. influenzae* corresponding to an orf with a high degree of similarity to the *E. coli* gene surA (FIG. 3E). In *E. coli* this gene is required for colony formation; thus, it is not surprising that insertions in surA are undetectable. Other regions were identified that were largely devoid of insertions but which did contain a few insertions, usually in specific reproducible locations. For example, the *H. influenzae* homologue of the *E. coli* secA gene (which encodes a portion of the preprotein translocase required for protein secretion) contained two clear insertions near the predicted 3' end of the gene (FIG. 3C, open arrowheads). This finding is consistent with the previous observation that *E. coli* containing a truncated secA gene are capable of survival.

Figure 3F:
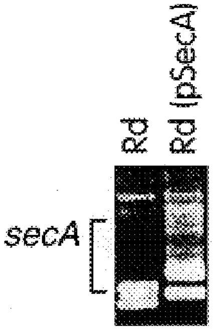

We tested whether the distribution of mariner insertions revealed by GAMBIT analysis reflects the essential nature of a given gene or simply site specificity of the transposon. To do this we performed in vitro mutagenesis of a chromosomal fragment which included the *H. influenzae* secA gene. The mutagenized DNA was then transformed into both wild-type *H. influenzae* (Rd) and an *H. influenzae* strain complemented with *E. coli* secA (RdpSecA). As discussed above, in the wild-type *H. influenzae* strain, no insertions could be found in the first 75% of the secA gene. However, when GAMBIT was performed on the same region in a strain complemented with *E. coli* secA, numerous transposon insertions could be found throughout the gene (FIG. 3F). These data provide strong evidence that gaps in the distribution of mariner insertions can be confidently attributed to the presence of an essential DNA sequence.

Using this method we studied five genomic segments in *H. influenzae* (FIG. 4) and two in *S. pneumoniae* (Table I), and identified several candidate genes required for growth or viability (FIG. 5). Many of these are known to be essential in other organisms, including secA, surA, tmk and Igt. Other genes have no previously known function.

Figure 4:
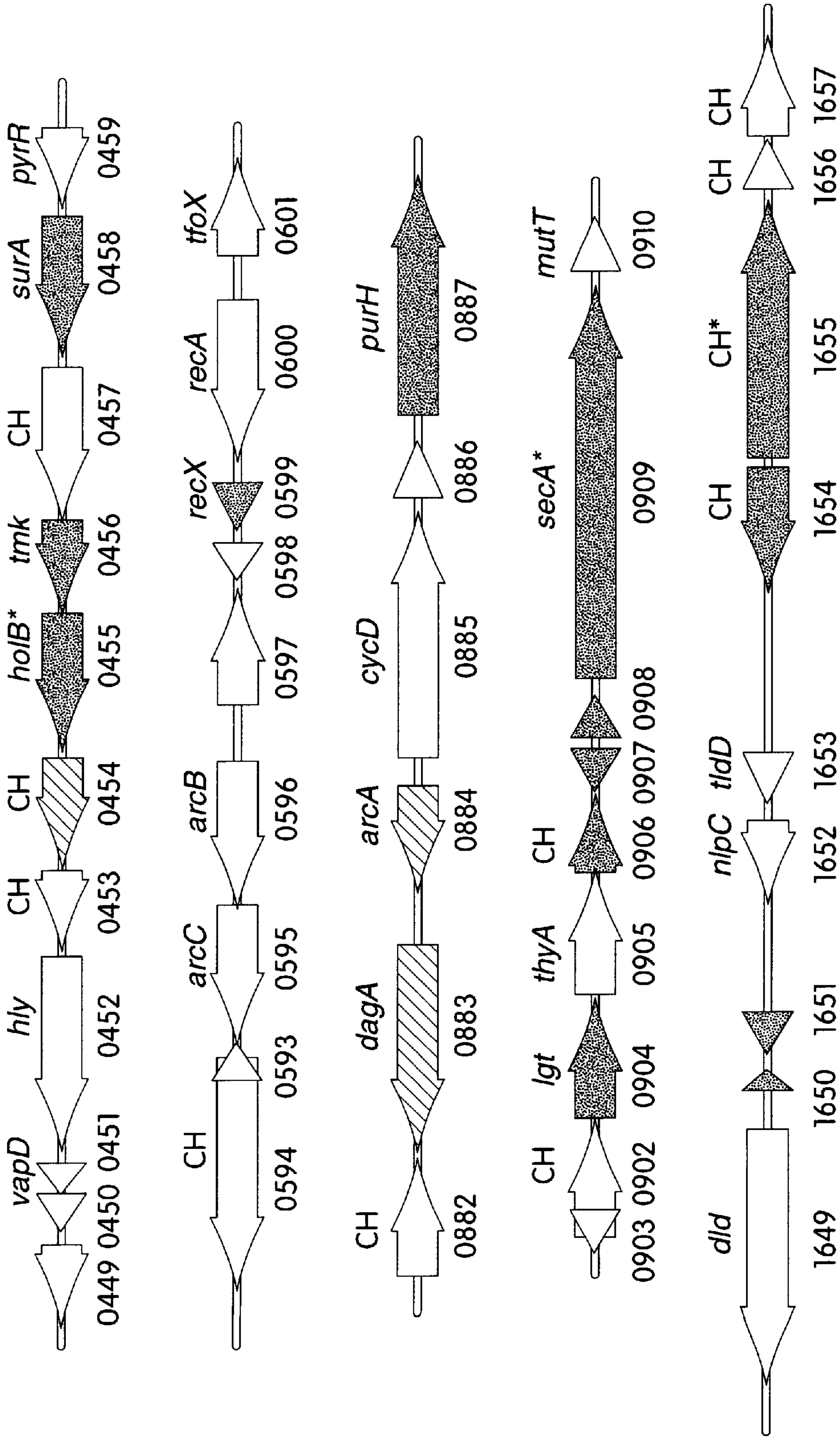
FIG. 4 shows *H. influenzae* orfs analyzed using in vitro transposition mutagenesis. Orfs with essential functions are shown in black, orfs that are non-essential are shown in white, and orfs in which mutations produce growth attenuation are shown in gray. The direction of transcription for each orf is shown along with the TIGR designation below the orf and the closest homologue above the orf. The * designates essential orfs which can sustain a very limited number of discrete insertions (<2/kbp). Conserved hypothetical orfs of unknown function are designated CH.

FIG. 4 shows the *H. influenzae* orf analysis. As in *S. pneumoniae* , orfs with essential functions were identified using the GAMBIT/mariner method (FIGS. 4 and 5).

An advantage of the GAMBIT technique is its ability to scan specific regions or, by more comprehensive projects, entire genomes for the presence of essential genes or DNA regions. Mutants that are reduced in growth, however, can also be detected by GAMBIT interrogation of a DNA region. Our analysis did, in fact, detect regions with partial reductions of band intensity, suggesting that mutants with insertions in these regions had reduced the growth rates but remained viable. For example, among the genes we studied were three genes of unknown

TABLE I

| S.p. orf* | Position† | Essential‡ | Similarity (GAP-BLAST E-value) |
|---|---|---|---|
| conserved hypothetical | 840–2174 | No | Archaeoglobus fulgidus hypo. protein, AF0170, (1e-47) |
| unknown | 3051–3866 | No | None |
| rbfA | 4109–4459 | Yes | *B. subtilis* Ribosome-binding factor A, P32731, (4e-20) |
| IF-2 | 4710–7586 | Yes | *H. influenzae* Translation initiation factor IF-2, P44323, (e-153) |
| L7AE | 7603–7902 | Yes | *Enterococcus faecium* Probable ribosomal protein in L7AE family, P55768, (6e-23) |
| nusA | 8210–9346 | Yes | *B. subtilis* NusA, Z99112, (3e-96) |
| p15A | 9390–9860 | No | *B. subtilis* P15A homolog, unknown function P32726, (2e-27) |
| ytmQ | 9995–10630 | No | *B. subtilis* YtmQ, unknown function, Z99119, (5e-73) |

TABLE I-continued

| S.p. orf* | Position† | Essential‡ | Similarity (GAP-BLAST E-value) |
|---|---|---|---|

Figure 3G:
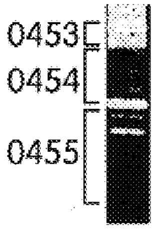

PCR Primers used to amplify the 11,266 bp corresponding to contig 4151 of TIGR *S. pneumoniae* genomic sequence release 112197 are:
Forward 5'-CTTTCTGTAAAATGTGGGATTCAA-3' (SEQ ID NO: 1); and
Reverse 5'-AATTATTATGAGTCGTCGTTTG-3' (SEQ ID NO:2).
†S.p. orf designations are based on matches giving the highest GAP-BLAST score.
‡Essential regions as defined in the text.

function which had been hypothesized to be members of the minimal gene set required by all bacteria. Two of these (HI0454 (see FIG. 3G) and HI1654 (not shown)) apparently cause growth attenuation when disrupted. GAMBIT analysis of HI0454 yielded detectable bands that were reduced in intensity, whereas HI1654 yielded no detectable bands. The third (HI0597), however, proved to be nonessential in *H. influenzae* under our in vitro conditions.

Figure 6:
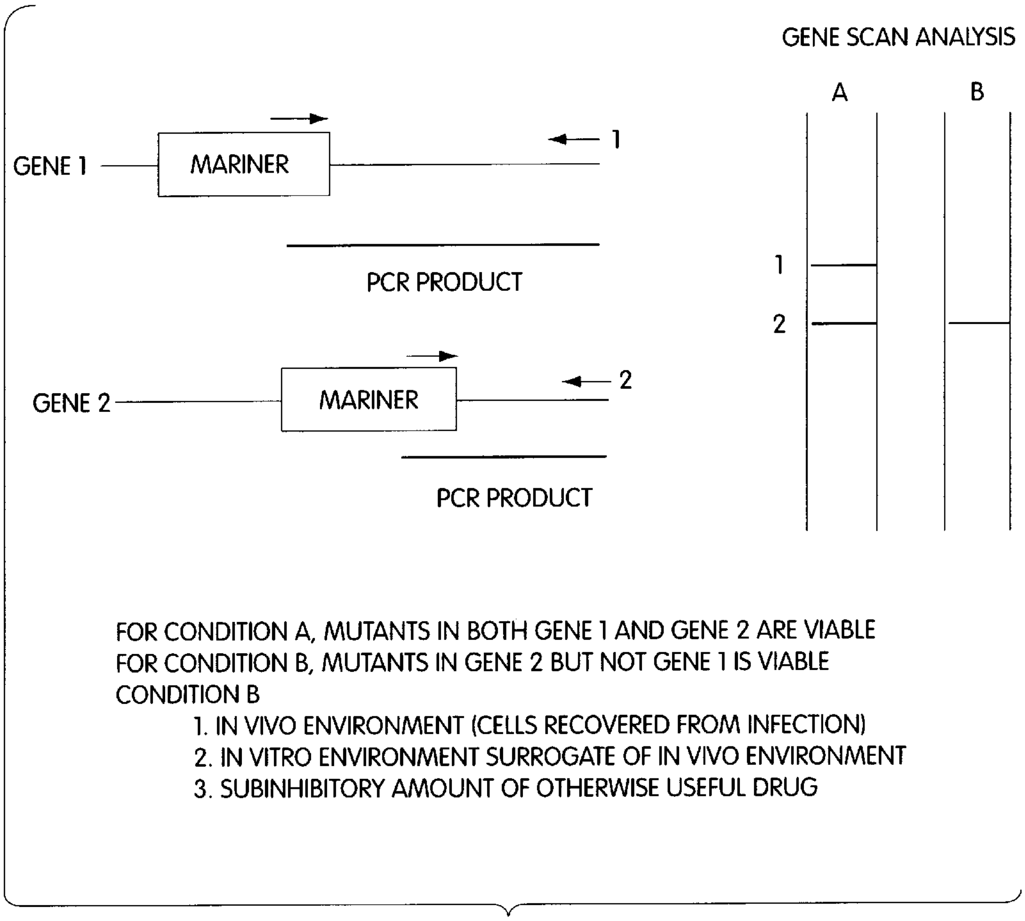
FIG. 6 shows a diagram depicting the identification of a gene that is essential for growth under stringent versus permissive growth conditions.

GAMBIT should prove equally useful for identifying genes required for growth or viability under specific growth conditions that are more stringent than the rich in vitro media used exclusively here. For example, GAMBIT should allow systematic identification of the genes required by pathogenic organisms to grow and survive within a host. FIG. 6 depicts the potential outcome of such a scenario. A pool or clone of transposon-mutagenized cells is grown under conditions A and B. Condition A represents a permissive growth environment, such as rich in vitro growth media. Condition B represents a stringent growth environment, such as growth in a host, or growth in an in vitro environment that simulates a host environment, or growth in the presence of a drug at a concentration that is sub-inhibitory for wild type cells. Cells that are mutant for hypothetical gene 1 or gene 2 are viable under rich growth conditions; but only cells that are mutant for gene 2 are viable under stringent growth conditions. Therefore, gene 1 is essential for growth under stringent conditions (e.g., in a host, or in the presence of drug), but is not essential under permissive (i.e., rich growth media) conditions.

GAMBIT is well-suited to the analysis of naturally competent organisms, a group which includes important human pathogens belonging to the genera Haemophilus, Streptococcus, Helicobacter, Neisseria, Campylobacter, and Bacillus. It is also apparent that, with the use of allelic replacement vectors or efficient linear DNA transformation methods, GAMBIT should be adaptable to other bacteria and microorganisms as well. For example, the genomes of bacterial pathogens such as: *Actinobacillus actinomycetemcomitans, Borrelia burgdorferi, Chlamydia trachomatis, Enterococcus faecalis, Escherichia coli, Haemophilus influenzae, Helicobacter pylori, Legionella pneumophila, Mycobacterium avium, Mycobacterium tuberculosis, Mycoplasma genitalium, Mycoplasma pneumonia, Neisseria gonorrhoeae, Neisseria meningitidis, Staphylococcus aureus, Streptococcus pneumoniae, Streptococcus pyogenes, Treponema pallidum*, and *Vibrio cholerae* are either partially or entirely sequenced. Such sequence information makes possible the use of GAMBIT for the identification of drug target genes in these organisms. Drug target genes may be exploited in screening assays for the identification and isolation of antimicrobial compounds.

In addition, promoters from essential genes identified by GAMBIT, when fused to reporter genes, may be used in sensitive high-throughput screens for the identification of compounds that decrease expression of essential genes at the transcriptional or post-transcriptional stages. Such screens are useful for the detection of antimicrobial compounds. Analogous screens for compounds that increase expression of essential genes also are useful, for example, for identifying compounds that increase expression of a gene that promotes survival (e.g., an anti-apoptotic gene) in an animal or plant cell. Alternatively, increased or decreased expression of essential genes identified by GAMBIT can be detected by other methods known to skilled artisans, such as by PCR or ELISA. In either case, the assays utilize standard molecular and cell biological techniques known to those skilled in the art. Such assays are readily adaptable to high-throughout screening assays for identifying or isolating novel compounds that regulate expression of essential genes.

Test Compounds and Extracts

In general, compounds are identified from large libraries of both natural product and synthetic (or semi-synthetic) extracts or chemical libraries according to methods known in the art. Those skilled in the field of drug discovery and development will understand that the precise source of test extracts or compounds is not critical to the screening procedure(s) of the invention. Accordingly, virtually any number of chemical extracts or compounds can be screened using the methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their anti-pathogenic activity should be employed whenever possible.

When a crude extract is found to have a desired modulating activity, or a binding activity, further fractionation of the positive lead extract is necessary to isolate chemical constituents responsible for the observed effect. Thus, the goal of the extraction, fractionation, and purification process is the careful characterization and identification of a chemical entity within the crude extract having the desired activity. Methods of fractionation and purification of such heterogenous extracts are known in the art. If desired, compounds shown to be useful agents for the treatment of pathogenicity are chemically modified according to methods known in the art.

Uses

For therapeutic uses, the compounds, compositions, or agents identified using the methods disclosed herein may be administered systemically, for example, formulated in a pharmaceutically-acceptable buffer such as physiological saline. Treatment may be accomplished directly, e.g., by treating the animal with antagonists which disrupt, suppress, attenuate, or neutralize the biological events associated with a pathogen. Preferable routes of administration include, for example, inhalation or subcutaneous, intravenous, interperitoneally, intramuscular, or intradermal injections which provide continuous, sustained levels of the drug in the patient. Treatment of human patients or other animals will be carried out using a therapeutically effective amount of an anti-bacterial agent in a physiologically-acceptable carrier. Suitable carriers and their formulation are described, for example, in Remington's *Pharmaceutical Sciences* by E. W. Martin. The amount of the anti-bacterial agent to be administered varies depending upon the manner of administration, the age and body weight of the patient, and with the type of disease and extensiveness of the disease. Generally, amounts will be in the range of those used for other agents used in the treatment of other microbial diseases, although in certain instances lower amounts will be needed because of the increased specificity of the compound. A compound is administered at a dosage that inhibits microbial proliferation or survival. For example, for systemic administration a compound is administered typically in the range of 0.1 ng–10 g/kg body weight.

For agricultural uses, the compounds, compositions, or agents identified using the methods disclosed herein may be used as chemicals applied as sprays or dusts on the foliage of plants, or in irrigation systems. Typically, such agents are to be administered on the surface of the plant in advance of the pathogen in order to prevent infection. Seeds, bulbs, roots, tubers, and corms are also treated to prevent pathogenic attack after planting by controlling pathogens carried on them or existing in the soil at the planting site. Soil to be planted with vegetables, ornamentals, shrubs, or trees can also be treated with chemical fumigants for control of a variety of microbial pathogens. Treatment is preferably done several days or weeks before planting. The chemicals can be applied by either a mechanized route, e.g., a tractor or with hand applications. In addition, chemicals identified using the methods of the assay can be used as disinfectants.

In addition, the antipathogenic agent may be added to materials used to make catheters, including but not limited to intravenous, urinary, intraperitoneal, ventricular, spinal and surgical drainage catheters, in order to prevent colonization and systemic seeding by potential pathogens. Similarly, the antipathogenic agent may be added to the materials that constitute various surgical prostheses and to dentures to prevent colonization by pathogens and thereby prevent more serious invasive infection or systemic seeding by pathogens.

Methods

Bacterial Culture

*H. influenzae* Rd strain (ATCC #9008) (J. Reidl and J. J. Mekalanos; *J. Exp. Med.* 183: 621–629 (1996)), the gift of Andrew Wright, was grown on BHI medium supplemented with 5% Levinthal's base (BXV) (H. Alexander, in: Bacterial and Mycotic Infections of Man, R. Dubos, J. Hirsch, Eds. (JB Lipincott, Philadelphia, 1965), vol. 724–741) or on MIc medium (R. M. Herriott, E. M. Meyer, M. Vogt, *J. Bacteriol.* 101: 517–524 (1970)).

*S. pneumoniae* (strain Rx1) (N. B. Shoemaker and W. R. Guild, *Mol. Gen. Genet.* 128: 283–290 (1974)) was grown on tryptic soy agar supplemented with 5% defibrinated sheep blood.

In Vitro Transposition

Minitransposons were constructed which contained the inverted repeats of the Himar transposon and ~100 bp of Himar transposon sequence flanking either a kanamycin resistance gene (M. F. Alexeyev, I. N. Shokolenko, T. P. Croughan. *Gene* 160: 63–67 (1995)) for *H. influenzae* or a chloramphenicol resistance gene (J. P. Claverys, A. Dintilhac, E. V. Pestova, B. Martin, D. A. Morrison. *Gene* 164: 123–128 (1995)) for *S. pneumoniae* . Transposition reactions were performed using purified Himar transposase as previously described (D. J. Lampe, supra; herein incorporated by reference).

Templates for transposition were either chromosomal DNA or PCR products. PCR of ~10 kb chromosomal regions was performed using Taq polymerase (Takara) and Pfu polymerase (Stratagene) at a 10:1 ratio, 100 pmol of primers and 30 cycles of amplification (30 seconds denaturation at 95° C., 30 seconds annealing at 62° C. and 5 minutes extension at 68° C. with 15 seconds added to the extension time for each cycle). Gaps in transposition products were repaired with T4 DNA polymerase and nucleotides followed by T4 DNA ligase with ATP (New England Biolabs) (J. Sambrook, E. F. Fritsch, T. Maniatis, Molecular Cloning-A Laboratory Manual, Second Edition, (Cold Spring Harbor Laboratory Press, Cold Spring Harbor, N.Y., 1989)).

Repaired transposition products were transformed into *H. influenzae* as previously described (G. J. Barcak, M. S. Chandler, R. J. Redfield, J. F. Tomb, *Meth. Enzymol.* 204:321–342 (1991)). and into *S. pneumoniae* as previously described using CSP-1 for competence induction (L. S. Havarstein, G. Coomaraswamy, D. A. Morrison; *Proc. Natl. Acad. Sci.* U.S.A. 92:11140–11144 (1995)).

Genomic Footprinting

Genomic footprinting was carried out as described (I. R. Singh, R. A. Crowley, P. O. Brown, *Proc. Natl. Acad. Sci.* U.S.A. 94: 1304–9, 1997; herein incorporated by reference) using a transposon-specific primer (5'-CCGGGGACTTATCAGCCAACC-3'; SEQ ID NO: 3) and primers specific to each chromosomal region designed using chromosomal sequence from The Institute for Genomic Research (TIGR). The chromosomal primers for the experiments shown in FIGS. 3A–3G lie within or near the following loci (TIGR designation):

a) HI0449 (primer in lane 1 (5'-CGCCTTTTTGTAAATCACGCATCGC-3'; SEQ ID NO: 4) hybridizes 114 bp 5' of the primer in lane 2 (5'-GCGGATGAAACAAATCGACCAGCAG-3'; SEQ ID NO: 5));

b) HI1658 (5'-TCACGCCGCTGATTTTGCTGG-3'; SEQ ID NO: 6);

c) HI0911 (5'-GGGAGCAAGAAAAGCGACAGAAGCC-3'; SEQ ID NO: 7);

d) HI0905 (5'-AAATCATCCATCGTGACCCA-3'; SEQ ID NO: 8);

e) HI0461 (5'-CCCGAATAAATTGCTTATCGCCTCG-3'; SEQ ID NO: 9);

f) HI0911 (5'-GGGAGCAAGAAAAGCGACAGAAGCC-3'; SEQ ID NO: 10); and g) HI0456 (5'-CAGGCGTATCAGGGTGGTGGACG-3'; SEQ ID NO: 11).

PCR was performed using the protocol described above. Potential *S. pneumoniae* orfs were analyzed for homology using the GAP-BLAST program (S. F. Altshul, T. L. Madden, A. A. Schaffer, J. Zhang, Z. Zhang, W. Miller, D. J. Lipman, *Nucleic Acids Res.* 25: 3389–3402, 1997).

PCR products were analyzed by gel electrophoresis on 0.8% agarose gels. Plasmid pSecA, which contains the *E. coli* secA gene, was constructed by cloning the BamHI fragment from pT7secA (M. G. Schmidt and D. B. Oliver; *J. Bacteriol.* 171: 643–9 (1989)), the gift of Carol Kumamoto, into the BglII site of the *E. coli-H. influenzae* shuttle plasmid pGJB103 (G. J. Barcak, M. S. Chandler, R. J. Redfield, J. F. Tomb, *Meth. Enzymol.* 204:321–42 (1991)), the gift of Gerard Barcak.

Isolation of Conditional Mutations in Essential Genes

Isolation of conditional mutations in essential genes represents a powerful next step in characterization of genes identified by GAMBIT. Temperature sensitive mutations are a class of functional mutations in protein coding regions that allow depletion of the active form of the non-permissive temperature.

We have begun analysis of essential genes identified by GAMBIT by isolating temperature sensitive mutations. Briefly, DNA containing a mariner insertion near an essential gene is amplified by mutagenic PCR (using standard PCR conditions modified by the addition of 125 $\mu$M $MnCl_2$ to the reaction) and transformed into *H. influenzae*. This mutagenesis method allows nucleotide misincorporation during amplification and is predicted to give a relatively high proportion of missence mutations in comparison with methods which induce DNA damage, such as UV irradiation, which leads to relatively high frequency of deletion mutations. In addition, since DNA damage is not generated by this procedure, second site mutations due to the induction of DNA repair mechanisms of the host cell are absent or greatly reduced in frequency.

*H. influenzae* transformants are selected on kanamycin and screened for growth at 30° C. and lack of growth at 37° C. The mutation is then mapped by rescuing growth at the non-permissive temperature via transformation with PCR products corresponding to the wild-type region being analyzed. By transforming with wild-type DNA it is possible to map the mutation to a specific open-reading frame. If necessary, further mapping can be accomplished by sequencing the mutant allele. Using this method we have isolated conditional lethal mutations in the *H. influenzae* secA homologue and in a conserved gene.

This set of techniques provides a rapid way to confirm essentiality and characterize genes identified by GAMBIT. The linked insertions generated by GAMBIT near each essential gene automatically provide the starting material for these experiments. Since cloning in recombinant plasmids is not necessary in naturally competent organisms, the method eliminates time-consuming steps that would be needed to generate complementing clones. At the same time, the method provides a strain in which the gene of interest can be selectively, and inducible depleted from the cell.

Conditional mutations of this kind can be used to further define the functions of essential genes. In addition, conditional mutations in essential genes can be used to produce cells with intermediate levels of the essential protein. These mutant may be used for drug sensitivity screens.

Other Embodiments

All publications mentioned in this specification are herein incorporated by reference to the same extent as if each independent publication was specifically and individually indicated to be incorporated by reference.

While the invention has been described in connection with specific embodiments thereof, it will be understood that it is capable of further modifications. This application is intended to cover any variations, uses, or adaptations following, in general, the principles of the invention and including such departures from the present disclosure within known or customary practice within the art to which the invention pertains and may be applied to the essential features hereinbefore set forth, and follows in the scope of the appended claims.

What is claimed is:

1. A method for locating an essential region in a portion of the genomic DNA from the genome an organism, said method comprising:

a) mutagenizing DNA having the sequence of said portion of genomic DNA, said mutagenizing using in vitro mutagenesis with a transposon, wherein said mutagenizing is sufficient to mutagenize a region of an essential gene, resulting in a transposon insertion frequency in said portion of genomic DNA of at least 3 insertions per kilobase of target DNA;

b) transforming cells of said organism with the mutagenized DNA of step a), wherein said cells have a haploid growth phase;

c) identifying cells containing said mutagenized DNA; and d) locating said essential region of said portion of genomic DNA by detecting the absence of transposons in said essential region in the mutagenized cells containing said mutagenized DNA.

2. The method of claim 1, wherein said portion of genomic DNA is amplified by PCR prior to mutagenesis.

3. The method of claim 1, wherein said portion of genomic DNA is cloned into a vector prior to in vitro transposon mutagenesis.

4. The method of claim 1, wherein said transposon contains a selectable marker.

5. The method of claim 1, wherein said transposon is mariner.

6. The method of claim 5, where said method further comprises the use of Himar 1 transposase.

7. The method of claim 1, wherein said locating of an essential region is done by performing PCR footprinting on a pool of transposon-mutagenized cells, wherein said PCR footprinting is performed using a primer that hybridizes to said transposon, plus a primer that hybridizes to a specific location on the target DNA, and wherein the products of said PCR are separated on a footprinting gel, wherein a PCR product on the gel represents a region of said chromosome that does not contain an essential gene, and wherein the lack of said PCR product in an area of the gel, where said PCR product is expected, represents a region of said target DNA that contains an essential gene, or, wherein a low level of said PCR product on the gel, relative to other PCR products on the gel, represents a region of said target DNA that contains an essential gene.

8. The method of claim 1, wherein prior to said transforming, said mutagenized DNA is subjected to gap repair using DNA polymerase and DNA ligase.

9. The method of claim 1, wherein the target cell is a single-cell microorganism.

10. The method of claim 1, wherein the cells are naturally competent for transformation.

11. The method of claim 1, wherein the cells are made competent prior to transformation with said mutagenized DNA.

12. The method of claim 1, wherein said organism is a fungus.

13. The method of claim 12, wherein said fungus is a yeast.

14. The method of claim 13, wherein said yeast is *Saccharomyces cerevisiae.*

15. The method of claim 9, wherein said microorganism is a bacterium.

16. The method of claim 15, wherein said bacterium is a gram-positive bacterium.

17. The method of claim 16, wherein said bacterium is selected from the group consisting of: *Actinobacillus acti-*

*nomycetemcomitans; Borrelia burgdorferi; Chlamydia trachomatis; Enterococcus faecalis; Escherichia coli; Haemophilus influenzae; Helicobacter pylori; Legionella pneumophila; Mycobacterium avium; Mycobacterium tuberculosis; Mycoplasma genitalium; Mycoplasma pneumonia; Neisseria gonorrhoeae; Neisseria meningitidis; Staphylococcus aureus; Streptococcus pneumoniae; Streptococcus pyogenes; Treponema pallidum*; and *Vibrio cholerae.*

18. The method of claim 1, wherein said mutagenized DNA is recombined into the genome of the target organism using an allelic replacement vector.

19. The method of claim 1, wherein said transposon contains a selectable marker gene, and wherein said identifying said cells containing said mutagenized DNA is based upon the ability of the transformed cells to grow on selective medium, wherein a cell containing a transposon can grow on said selective medium, and a cell lacking a transposon cannot grow, or grows more slowly, on said selective medium.

20. The method of claim 1, wherein said transposon contains a reporter gene, wherein said identifying of said cells containing said mutagenized DNA is based on a reporter gene assay, wherein a cell comprising a transposon expresses said reporter gene and a cell lacking a transposon does not express said reporter gene.

21. The method of claim 1, wherein said in vitro mutagenesis is high saturation mutagenesis.

22. The method of claim 1, wherein said insertion frequency is at least 8 insertions per kilobase of target DNA.

* * * * *

UNITED STATES PATENT AND TRADEMARK OFFICE

CERTIFICATE OF CORRECTION

PATENT NO. : 6,207,384 B1 
DATED : March 27, 2001
INVENTOR(S) : John J. Mekalanos et al.

It is certified that error appears in the above-identified patent and that said Letters Patent is hereby corrected as shown below:

Title page,
Item [56], OTHER PUBLICATIONS, “Reidl et al., reference,” replace “e(p4)” with -- e(P4) --;

Column 10,
Line 34, replace “Igt” with -- lgt --;
Line 37, replace “*S. Pneumoniae*,” with -- *S. Pneumoniae*, --;

Column 11,
Line 9, replace “Reverse 5’-AATTATTATGAGTCGTCGTTTG-3’” with -- Reverse 5’-AATTATTATGGAGTCGTCGTTTGG-3 --;
Line 10, replace “†S.p.” with -- *S.p. --; and
Line 10, insert a new line after “….GAP-BLAST score.” that reads -- † Positions are given with respect to the first base of the Forward primer. --.

Signed and Sealed this

Third Day of June, 2003

JAMES E. ROGAN
*Director of the United States Patent and Trademark Office*